United States Patent
Wells et al.

(10) Patent No.: US 10,889,785 B2
(45) Date of Patent: Jan. 12, 2021

(54) COMPOSITIONS AND METHODS FOR REDUCING CAT ALLERGENS IN THE ENVIRONMENT

(71) Applicant: Nestec S.A, Vevey (CH)

(72) Inventors: George Wells, St. Louis, MO (US); Delphine Tissot-Favre, Gollion (CH); Ebenezer Satyaraj, Wildwood, MO (US); Juergen Eck, Bensheim (DE); Daniel Meyer, Schenkon (CH); Torsten Ertongur-Fauth, Darmstadt (DE); Alexander Pelzer, Bickenach (DE); Scott Sherrill, Chesterfield, MO (US); Peichuan Sun, St. Louis, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 0 days.

(21) Appl. No.: 15/945,131

(22) Filed: Apr. 4, 2018

(65) Prior Publication Data

US 2018/0223223 A1 Aug. 9, 2018

Related U.S. Application Data

(63) Continuation of application No. 14/570,310, filed on Dec. 15, 2014, now abandoned.

(60) Provisional application No. 61/918,420, filed on Dec. 19, 2013.

(51) Int. Cl.
| | | |
|---|---|---|
| *C11D 3/386* | (2006.01) | |
| *C11D 11/00* | (2006.01) | |
| *A23K 20/189* | (2016.01) | |
| *A23K 50/40* | (2016.01) | |
| *A23K 50/42* | (2016.01) | |
| *A23K 50/48* | (2016.01) | |
| *A01K 1/015* | (2006.01) | |
| *A61L 9/00* | (2006.01) | |
| *A61K 38/00* | (2006.01) | |

(52) U.S. Cl.
CPC ........ *C11D 3/38609* (2013.01); *A01K 1/0155* (2013.01); *A23K 20/189* (2016.05); *A23K 50/40* (2016.05); *A23K 50/42* (2016.05); *A23K 50/48* (2016.05); *A61L 9/00* (2013.01); *C11D 3/386* (2013.01); *C11D 3/38618* (2013.01); *C11D 11/0011* (2013.01); *A61K 38/00* (2013.01); *C12Y 304/21062* (2013.01)

(58) Field of Classification Search
CPC ............ C11D 11/0011; C11D 3/38609; C12Y 304/21062
See application file for complete search history.

(56) References Cited

U.S. PATENT DOCUMENTS

| | | |
|---|---|---|
| 5,679,630 A | 10/1997 | Baeck et al. |
| 5,826,546 A | 10/1998 | Epstein |
| 7,704,532 B1 | 4/2010 | Smith |
| 2002/0176854 A1 | 11/2002 | Payton |
| 2004/0007251 A1 | 1/2004 | Koenig et al. |
| 2006/0142394 A1 | 6/2006 | Kapitz et al. |
| 2007/0196353 A1 | 8/2007 | Payton |
| 2008/0124297 A1 | 5/2008 | Payton |
| 2008/0244853 A1 | 10/2008 | Koenig et al. |
| 2009/0175896 A1 | 7/2009 | Bachmann et al. |
| 2009/0247443 A1* | 10/2009 | Lane ..................... A61L 12/082 510/100 |
| 2011/0135750 A1 | 6/2011 | Bylemans |

FOREIGN PATENT DOCUMENTS

| | | |
|---|---|---|
| EP | 0425018 A1 | 2/1991 |
| JP | 11-9202 A | 1/1999 |
| JP | 2004-196763 A | 7/2004 |
| JP | 2005-508361 A | 3/2005 |
| JP | 2005-513007 T | 5/2005 |
| JP | 2005-287411 A | 10/2005 |
| RU | 2414239 C2 | 3/2011 |
| WO | 2004007658 A2 | 1/2004 |
| WO | 2007113633 A2 | 10/2007 |
| WO | 2009009061 A1 | 1/2009 |
| WO | 2010030058 A1 | 3/2010 |

OTHER PUBLICATIONS

Neidhart et al, The refined crystal structure of subtilisin Carlsberg at 2.5 A resolution. Protein Eng. Oct. 1988;2(4):271-6.*

Pagan et al, On the Role of Protein Structural Dynamics in the Catalytic Activity and Thermostability of Serine Protease Subtilisin Carlsberg. Biotechnology and Bioengineering, vol. 103, No. 1, May 1, 2009 p. 77-84.*

Barrett et al, 550. Subtilisins. In: Handbook of Proteolytic Enzymes Second Edition vol. 2, p. 1786-87.*

Counsell et al, Allergens, IgE, mediators, inflammatory mechanisms; Definition of the human T-cell epitopes of Fel d 1, the major allergen of the domestic cat. J Allergy Clin Immunol vol. 98, No. 5, Part 1.*

Van Ree, et al, "Purified natural and recombinant Fel d 1 and cat albumin in in vitro diagnostics for cat allergy," J Allergy Clin Immunology, 1999, vol. 104 No. 6, pp. 1223-1230, the Netherlands.

Kleine-Tebbe et al., Role of the Major Allergen (Fel d 1) in Patients Sensitized to Cat Allergens, Int. Arch. Allergy Immunol. 1993, 100:256-262.

Valenta et al., "Recombinant allergen molecules: tools to study effector cell activation," Immunological Review 2001 vol. 179 119-127 Denmark.

(Continued)

*Primary Examiner* — Sheridan Swope

(57) ABSTRACT

Formulations, compositions and products for reducing allergenic Fel d 1 from the environment are disclosed. The formulations include at least one protease that interacts with the Fel d 1 and substantially degrades allergenic epitopes on the Fel d 1. Methods of using the formulations for reducing or eliminating allergenic Fel d 1 from the environment are also disclosed.

13 Claims, 9 Drawing Sheets

(56) References Cited

OTHER PUBLICATIONS

Aalberse, Rob C., "Structural biology of allergens" J Allergy Clin Immunol, 2000, vol. 106, No. 2. 228-238 the Netherlands.

Bartholome et al., "Where does cat allergen 1 come from?" J Allergy Clin Immunol. 1985, vol. 76, No. 3, pp. 503-506 West Germany and US.

Charpin et al., "Fel d 1 allergen distribution in cat fur and skin" J Allergy Clin Immunol, 1991, vol. 88, No. 1 pp. 77-82, France.

Dabrowski et al., "Cat skin as an important source of Fel d 1 allergen" 1990 J Allergy Clin Immunol, vol. 86, No. 4, Part 1, pp. 462-465, France.

Anderson et al., "A comparative study of the allergens of cat urine, serum, saliva, and pelt" 1985 J Allergy Clin Immunol, vol. 76, No. 4 pp. 563-568, US.

Van Milligen et al., "Presence of Felis domesticus Allergen I in the Cat's Salivary and Lacrimal Glands" Int Arch Allergy Applied Immunol 1990 92: 375-378 the Netherlands.

Geaney et al., A review of Allergen Avoidance Does not Alter Airborne Cat Allergen Levels in Classrooms, Pediatrics 2005 116:543 US.

Berge, et al., "Concentrations of cat (Fel d1) dog (Can f1) and mite (Der f1 and Der p1) allergens in the clothing and school environment of Swedish schoolchildren with and without pets at home", Pediatr.Allergy Immun. 1998 9(1):25-30 Norway.

Scarlett et al. "Reasons for Relinquishment of Companion Animals in US Animal Shelters: Selected Health and personal issues" Journal of Applied Animal Welfare Science 1999 2:1 41-57.

LGH Koren, E Janssen, A Willemse, American Academy of Allergy and Immunology Mar. 1995 Annual Meeting, Eindhoven & Utrecht, Netherlands https://allerpet.com/allerpet-study-abstract/.

Wang, et al., "Preparation of High F-Value Oligopeptides from Corn Gluten Meal and its Anti-fatigue Functions," International Conference on Biomedical Engineering and Biotechnology, 2012, China.

Szymkiewicz, et al. "Examination of Immunogenic Properties of Hydrolysed Milk and Pea Proteins—Application of Immunoblotting Technique" Polish Journal of Food and Nutrition Sciences, Poland, 2003 vol. 12/53, SI 1 pp. 79-83.

Wroblewska, et al., Immunoreactive properties of peptide fractions of cow whey milk proteins after enzymatic hydrolysis, International Journal of Food Science and Technology, Poland, 2004, 39, 839-850.

International Search Report & Written Opinion, Application No. PCT/IB2014/066936 dated Feb. 20, 2015.

Kristensen et al., Determinationof Isoforms et al., Aug. 1997, Biolog. Chem. vol. 378, pp. 899-908.

Kaiser, L et al., The crystal structure of the major cat allergen Fel d 1, a member of the secretoglobin family, J. Biol. Chem. 278, 37730-37735 2003.

Kaiser, L et al., Structural characterization of the tetrameric form of the major cat allergen Fel d 1, J. Mol. Biol. 370(4)714:27 2007.

\* cited by examiner

COMPOSITIONS AND METHODS FOR REDUCING CAT ALLERGENS IN THE ENVIRONMENT

CROSS REFERENCE TO RELATED APPLICATIONS

This application claims priority to U.S. application Ser. No. 14/570,310 filed Dec. 15, 2014 that claims priority to U.S. Provisional Application Ser. No. 61/918,420 filed Dec. 19, 2013, the disclosures of which are incorporated in its entirety herein by this reference.

BACKGROUND OF THE INVENTION

Field of the Invention

The invention relates generally to reducing or preventing cat allergies or their symptoms, and specifically to compositions and methods for reducing the major cat allergen, Fel d 1, from the environment.

Description of the Related Art

Domestic cats produce some of the most potent elicitors of allergic reaction, affecting people worldwide. The severity of symptoms ranges from mild rhinitis and conjunctivitis to life-threatening asthmatic responses. The most prominent and potent allergen in cat dander is Fel d 1. Fel d 1 elicits IgE responses in 90-95% of patients with cat allergy (van Ree et al., 1999, J. Allergy Clin. Immunol. 104: 1223-1230) and accounts for 60-90% of the total allergenic activity in cat dander (Kleine-Tebbe, et al., 1993 Int. Arch. Allergy Immunol. 100: 256-262).

The three-dimensional structures of only a few allergens have been reported (see Valenta & Kraft, 2001, Immunol. Rev. 179: 119-127). The biological functions of these allergens are diverse or unknown, without any particular biological or structural feature that seems to predispose a protein to act as an allergen (see Aalberse, 2000, J. Allergy Clin. Immunol. 106: 228-238). Protein structural features believed to be relevant for allergenicity include solubility, stability, size, and compactness of protein. These aspects reflect dependency of allergenicity on transport over mucosal barriers and susceptibility to proteases (Aalberse, 2000, supra). Posttranslational modification may also affect allergenicity, such as by introducing new epitopes or altering solubility, stability, size, susceptibility toward proteases, and/or uptake and processing by antigen-presenting cells (Aalberse, 2000, supra). Although glycosylation affects many of these processes, it is not determinative of allergenicity in and of itself. Many allergens are not glycosylated, whereas some are heavily glycosylated (Aalberse, 2000, supra). As a result, determination of the basis for allergenicity may require a detailed structural study of the allergen, and even that may not yield definitive results.

Fel d 1 is a 35-kDa tetrameric glycoprotein formed by two heterodimers. Each 18-kDa dimer is composed of two covalently linked chains derived from two independent genes, chain 1, comprising 70 residues, and chain 2 (of which there are two isoforms), comprising 90 or 92 residues. The three-dimensional structure of Fel d 1 has been determined (Kaiser et al., 2003, J. Biol. Chem. 278: 37730-37735, Kristensen et al., 1997, Biol. Chem. 378: 899-908). The fold of the protein was found to bear a striking resemblance to that of uteroglobin, a steroid-inducible, cytokine-like molecule with anti-inflammatory and immunomodulatory properties. The relative localization of three IgE epitopes was determined on the molecular surface of Fel d 1, at residues 15-28 (chain 2), 117-130, and 138-151 (chain 1), respectively (Kaiser et al., 2003, supra).

Fel d 1 is produced by sebaceous glands and squamous epithelial cells and is transferred to the fur by licking and grooming (Bartholome et al., 1985, J. Allergy Clin. Immunol. 76: 503-506; Charpin et al., 1991, J. Allergy Clin. Immunol. 88: 77-82; Dabrowski et al., 1990, J. Allergy Clin. Immunol. 86: 462-465). Fel d 1 is also present in the salivary, perianal, and lachrymal glands (Anderson et al., 1985, J. Allergy Clin. Immunol. 76: 563-569; van Milligen et al., 1990, Int. Arch. Allergy Appl. Immunol. 92: 375-378). Thus, the allergen is present within and on the animal, and is also carried by small airborne particles to surfaces within the environment occupied by the cat.

Strategies developed for controlling the reactions to such allergens include establishing tolerance to the allergen in an individual, and simple avoidance. Tolerance strategies entail establishment or reestablishment of a less harmful or more productive responses to exogenous allergens. Tolerance-inducing strategies traditionally have involved allergen immunotherapy, wherein the sensitized individual is intentionally exposed to the allergen in a controlled manner, for example through a series of injections, or through oral or nasal absorption. Immunotherapy has been in use for over 100 years, and has been successful, although it may take years to establish an acceptable level of tolerance. While potentially effective in the specific individual receiving the treatment, tolerance strategies are expensive, invasive, time-consuming, and require experts such as doctors, immunologists, and the like, for administration. Treatments for tolerance also involve a certain level of risk associated with adverse reactions and negative outcomes.

Avoidance of Fel d 1 is attractive in principle, but difficult to achieve. A study of households with cats indicated that Fel D1 is widely present, e.g., in 96.6% of the beds, 96.9% of bedroom floors, 96.1% of living room floors, and 97.9% of sofas. (Geany et al., *Pediatrics,* 116(2): August 2005). Clothing from school children from homes containing cats was tested outside of the home (in schools), and found to contain Fel D1 antigens.

Thus, this environmental antigen poses a substantial risk, not only to sensitized individuals living in households with cats, but to the allergic human population on the whole. (Gerge & Dreborg, *Ped. Allergy Immun.,* 9(1):25-30, 1998). As a result, while cat ownership is on the rise in the United States, allergies to cats have become and remain the primary reason for relinquishment of cats to animal shelters (Scarlett et al., 1999, J. Appl. Animal Welfare Sci. 2:41-57).

Though complete avoidance of Fel dl may not be practicable, a reduction in the amount of Fel d 1, even a minimal reduction, could have substantial impact on the health of sensitized individuals. This could minimize relinquishment as a result of a person in the home becoming sensitized.

Attempts have been made to reduce cat allergens from the environment. For instance, U.S. Pat. No. 7,704,532 discloses methods purported to mitigate allergic reactions in humans and other susceptible animals by directly contacting the allergens, including cat allergens, with a composition containing an acidic salt solution, including salts of aluminum, calcium and/or magnesium, to clothing, surfaces, interiors, furniture, plant bedding, plants and the like. U.S. Pat. No. 5,826,546 discloses a waterless method for shampooing a pet comprising using a foamable shampoo composition in combination with a dispenser capable of dispensing the composition as a foam. The composition may contain one or more of: anionic detergents, nonionic detergents, amphoteric detergents, preservatives, antimicrobial agents, antioxidants, mild soaps, surfactants, skin conditioners such as aloe extracts, fragrances, agents for treating flea infestation such as *melaleuca* oil, a pH adjuster such as citric acid, depending on the particular need of the pet. U.S. 2011/0135750 discloses methods and compositions purported to denature allergens, such as cat Fel d 1, the composition comprising a combination of calcium salts and lanthanum salts. U.S. 2004/0007251 discloses wet and dry wipe cleaners comprising an additive, such as a lectin, a protease and/or an enzyme inhibitor purportedly capable of binding to or cleaving an allergen, such as cat Fel d 1, and removing it from a surface. U.S. 2006/0142394 discloses methods for inhibiting dust mite feces and denaturing animal hair keratin and/or plant pollen or spores using composition comprising an enzyme capable of breaking down polypeptides such that they cannot elicit an allergenic effect on humans. U.S. Pat. No. 8,454,953 discloses methods for reducing or preventing allergies or symptoms of allergic reactions to allergens comprising contacting the source of the allergen with a composition comprising a molecule capable of inhibiting the ability of the allergen to bind to mast cells in an animal predisposed to having an allergic response. The molecule can be an antibody specific for the allergen, such as an antibody specific for the cat Fel d 1 allergen.

Various commercially available products and methods also purport to reduce allergens from the environment. One such method, said to be useful for prevention or mitigation of allergic reactions in humans, including those caused by cat Fel d 1, is performed by first cleaning surfaces in the environment and then applying a water-based solution that contains an ingredient derived from fruit and vegetable seed extracts, using a spray applicator to surfaces such as mattresses, carpeting, upholstered furniture, rugs and window treatments (see MASTERBLEND® Special Report on RESPONSIBLECARE SYSTEM™ ALLERGY RELIEF TREATMENT™, url masterblend.net). APDC, Inc. (url apdc-inc.com) produces the ALLER-RX® Anti-Allergen Spray, which is a liquid composition said to be derived from plants and naturally occurring organic compounds, containing chlorine dioxide. Another method involves directly applying a composition comprising shampoo and skin conditioning ingredients directly to an animal to remove allergens, including cat Fel d 1, on the animal's fur and skin (see ALLERPET™, produced by Allerpet, Inc., New York, N.Y.). Direct application of the composition to a cat was shown to reduce the amount of Fel d 1 on the cat's fur and on the carpet that was exposed to the cats (LGH Koren, E Janssen, A Willemse, American Academy of Allergy and Immunology March 1995 Annual Meeting, Eindhoven & Utrecht, Netherlands).

Though, as summarized above, certain methods and compositions are available in the art, there remains a need for additional and improved methods for reducing Fel d 1 in the environment or rendering it less allergenic or non-allergenic. There is also a need for compositions that allow sufficient control of the level and/or potency of Fel d 1 to reduce, minimize, or prevent an allergic response in individuals predisposed to having such a response.

SUMMARY OF THE INVENTION

It is, therefore, an object of the present invention to reduce or eliminate allergenic Fel d 1 from an environment.

It is a further object of the invention to reduce or eliminate allergenic Fel d 1 from environments comprising the local environment of an individual who may suffer from cat allergies.

It is yet a further object of the invention to reduce or eliminate allergenic Fel d 1 from sources of the allergen, e.g., cat hair, skin or fur, or cat saliva.

One or more of these other objects can be achieved using formulations, products, kits and methods comprising protease enzymes that interact with Fel d 1 and substantially degrade allergenic epitopes on the Fel d 1, thereby reducing or eliminating its allergenicity.

Other and further objects, features, and advantages of the present invention will be readily apparent to those skilled in the art.

DETAILED DESCRIPTION OF THE INVENTION

Definitions

Figure 1:
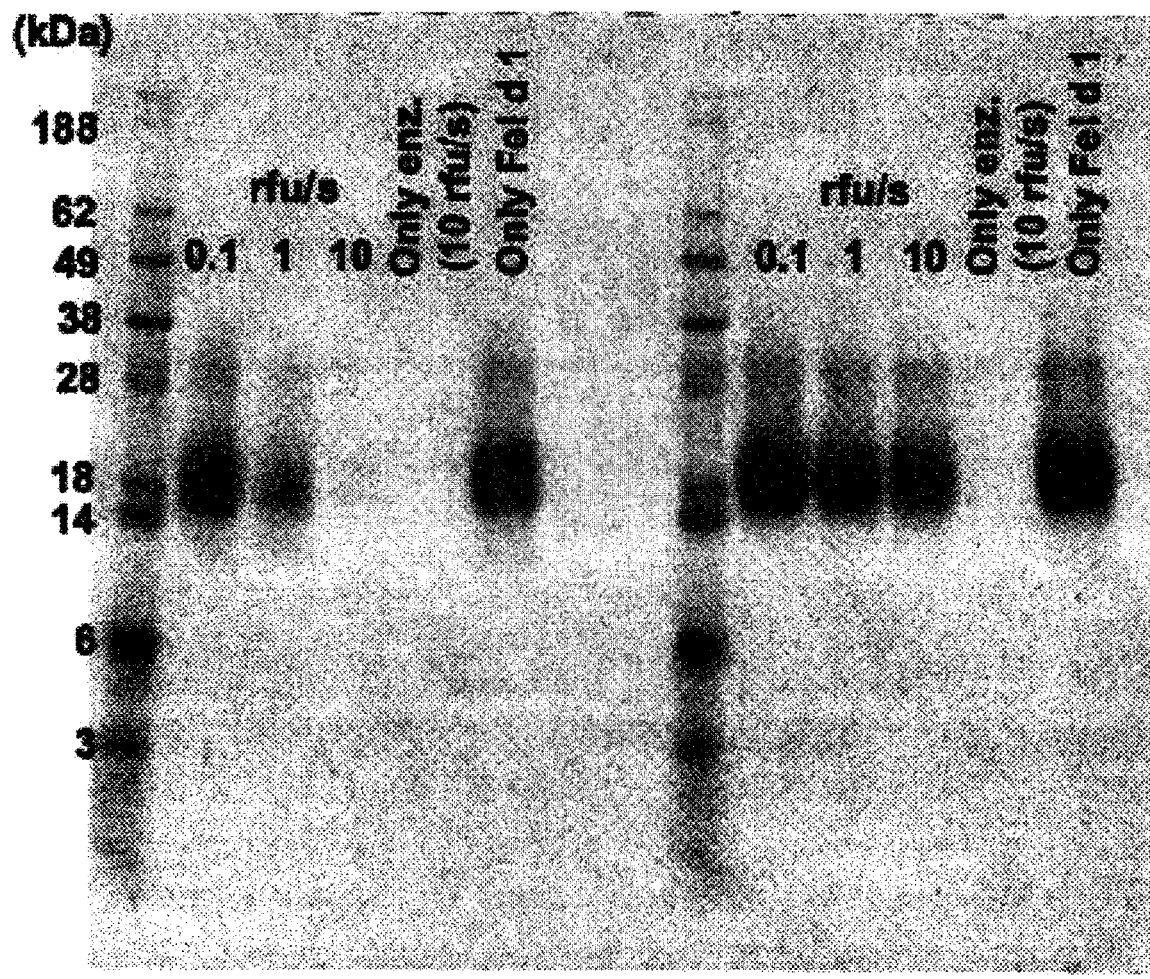
FIG. 1. SDS-PAGE showing that Fel d 1 is completely degraded by a *Bacillus licheniformis* subtilisin. Natural Fel d 1 (1.9 µg) was incubated overnight with 0.1, 1 or 10 rfu s$^{-1}$ of *Bacillus licheniformis* subtilisin (Alcalase®, Novozymes) activity at 37° either in Tris/HCl buffer (200 mM, pH 7.8) (left side of gel) or ammonium acetate buffer (100 mM, pH 4.0) (right side of gel). The subtilisin (10 rfu s$^{-1}$) without Fel d 1 and Fel d 1 without the subtilisin served as controls.

As used herein, the term "allergy" is synonymous with "allergic response" or "allergic reaction". Each of the terms refers to a state of immune responsiveness in an animal specific to an exogenous antigen (or "allergen") that is not otherwise harmful to the animal. A "symptom" of an allergic response refers to any measure of the aforesaid immune responsiveness, e.g. on the molecular level (including measurement of a activity or expression of a protein, or transcript or gene), the cellular level, organ level, systemic level, or organism level. Such symptoms can comprise one or more such levels. Symptoms may include generalized phenomena such as inflammation, respiratory complaints, swelling, or distress typically associated with allergy, rhinitis, edema, and allergic skin disorders including but not limited to atopic dermatitis (e.g. eczema), urticaria (e.g. hives) and angioedema, and allergic contact dermatitis. More specific phenomena that are "symptoms" of an allergic response include any measurable or observable change, for example at the cellular level, including but not limited to local or systemic changes in cell populations, eosinophilia, recruitment and/or activation of immune cells, including, for example, mast cells and/or basophils, changes in antigen-presenting cells (including but not limited to FcεRI-bearing dendritic cells), intracellular or molecular changes, including measurement or observations of one or more steps in an immunological cascade, release of intracellular compounds that mediate an allergic response (e.g. mediators), and changes in one or more cytokines (e.g. IL-3, IL-5, IL-9, IL-4, or IL-13) or related compounds or antagonists thereof. The skilled artisan will understand that certain symptoms as defined herein as more readily measured than others, and some are measured through subjective assessment or self-assessment of the symptom. For other symptoms, there are convenient or rapid assays or measurements for objectively assessing changes.

The term "environment" as used herein has three components as they relate to the cat allergen Fel d 1. These are sometimes referred to as "around the cat," "on the cat" and "in the cat." The environment "around the cat" refers to a local environment of an individual who may suffer from cat allergies, and/or a local environment inhabited by a cat. For example a house, room, car, office, hotel, yard, garage, and the like, could each be "environments" as used herein. Any inanimate surface on which an allergen may be disposed is considered part of the environment. Airborne particles containing the allergen are also considered part of the environment. Although environments around the cat are frequently indoors, nothing herein precludes a limited area partially or completely open or outdoors to be an environment, for example a patio, deck, landing, lanai, gazebo, porch, or the like can constitute an environment for purposes herein. The environment can also comprise a part or all of an animal that is the source of an allergen, e.g., the cat's skin, fur or saliva on the cat's skin or fur ("on the cat") or the cat's oral cavity or saliva therein ("in the cat").

As used herein, an "individual" means an individual animal of any species or kind, including a human.

With respect to kits, the term "single package" means that the components of a kit are physically associated in or with one or more containers and considered a unit for manufacture, distribution, sale, or use. Containers include, but are not limited to, bags, boxes or cartons, bottles, packages of any type, design, or material, over-wrap, shrink-wrap, affixed components (e.g. stapled, adhered, or the like), or combinations of any of the foregoing. For example, a single package kit may provide containers of individual compositions and/or food compositions physically associated such that they are considered a unit for manufacture, distribution, sale, or use The term "virtual package" means that the components of a kit are associated by directions on one or more physical or virtual kit components instructing the user how to obtain the other components, e.g., in a bag or other container containing one component and directions instructing the user to go to a website or personal device application ("app"), contact a recorded message or a fax-back service, view a visual message, or contact a caregiver or instructor to obtain, for example, instructions on how to use the kit, or safety or technical information about one or more components of a kit. Examples of information that can be provided as part of a virtual kit include instructions for use; safety information such as material safety data sheets; poison control information; information on potential adverse reactions; clinical study results; dietary information such as food composition or caloric composition; general information on physical activity, exercise, metabolism, endurance and the like.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

Ranges are used herein in shorthand, so as to avoid having to set out at length and describe each and every value within the range. Any appropriate value within the range can be selected, where appropriate, as the upper value, lower value, or the terminus of the range.

Where used herein, the term "about" indicates that the given value, plus or minus 20% or 15% or 10% or 5% or 1%, is intended. "About" is thus used a shorthand to reflect the recognition that small variations from the literal value stated are still within the scope of the invention.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a cat", "a method", or "a product" includes a plurality of such "cats", "methods", or "products". Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein "examples," or "for example," particularly when followed by a listing of terms, is merely exemplary and illustrative, and should not be deemed to be exclusive or comprehensive.

The term "comprising" is intended to include embodiments encompassed by the terms "consisting essentially of" and "consisting of". Similarly, the term "consisting essentially of" is intended to include embodiments encompassed by the term "consisting of".

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to and does not limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by the controlling law. The discussion of those references is intended merely to summarize the assertions made therein. No admission is made that any such patents, patent applications, publications or references, or any portion thereof, is relevant, material, or prior art. The right to challenge the accuracy and pertinence of any assertion of such patents, patent applications, publications, and other references as relevant, material, or prior art is specifically reserved.

EMBODIMENTS OF THE INVENTION

Compositions, methods, articles of manufacture, kits and packages are provided for reducing or eliminating the cat allergen Fel d 1 from the environment. The invention springs in part from the inventors' discovery that certain enzymes, particularly proteolytic enzymes (proteases), are able to degrade the antigenic epitopes from Fel d 1, thereby reducing or eliminating its allergenic effect.

One aspect of the invention features a formulation for reducing or eliminating allergenicity of Fel d 1, comprising at least one protease that interacts with the Fel d 1 and substantially degrades allergenic epitopes on the Fel d 1. The effective proteases are selected from serine proteases, thiol proteases, aspartyl proteases, zinc metalloproteases, or any combination thereof.

In certain embodiments, the serine proteases include subtilisin, proteinase K, trypsin, alpha-chymotrypsin, endoproteinase Glu-C and endoproteinase Lys-C. If subtilisin is used, it may be sourced from a species of *Bacillus* selected from *B. licheniformis, B. clausii, B. haloudurans, B. lentus, B. amyloliquefaciens, B. subtilis* or any combination thereof. The thiol proteases can include bromelain, papain and ficin, which are obtained from plant sources, e.g., pineapple, papaya and fig plants. The aspartyl proteases can include bovine chymosin, endothiapepsin (e.g., from *Chryphonectria parasitica*), mucorpepsin/rennin (e.g., from *Mucor miehei*) pepsin (e.g., of porcine origin) and aspergillopepsin (e.g., from *Trichoderma reesei, Aspergillus niger* or *Aspergillus oryzae*). The zinc metalloproteases can include thermolysin (e.g., from *Bacillus thermoproteolyticus rokko* or *Geobacillus* sp.) and endoproteinase Asp-N, (e.g., from *Flavobacterium meningosepticum*).

Table 1 below sets forth proteases suitable for use in the present invention. The proteases may be purified from a biological source or they can be obtained from commercial sources. Certain exemplary commercial sources are shown in the table; many others are available.

TABLE 1

| Functional Class | Exemplary Protease Tradename | Origin, Natural Source | Recommended name (IUPAC) | Enzyme Classification # (IUPAC) | EINECS # | CAS # |
|---|---|---|---|---|---|---|
| Serine Protease | Alcalase ® 2.4L (NZ) | *Bacillus licheniformis* | Subtilisin | 3.4.21.62 | 232-752-2 | 9014-01-1 |
| | Savinase ® 16.0L; Everlase ® 16.0L (NZ) | *Bacillus clausii* | Subtilisin | 3.4.21.62 | 231-752-2 | 9014-01-1 |
| | Esperase ® 8.0L (NZ) | *Bacillus haloudurans* | Subtilisin | 3.4.21.62 | 231-752-2 | 9014-01-1 |
| | Purafect ® (G) | *Bacillus lentus* | Subtilisin | 3.4.21.62 | 232-752-2 | 9014-01-1 |
| | Protex ® 6L; Protex ® 8L (G) | *Bacillus licheniformis* | Subtilisin | 3.4.21.62 | 231-752-2 | 9014-01-1 |
| | Protex ® 7L (G) | *Bacillus amyloliquefaciens* | Subtilisin | 3.4.21.62 | 232-752-2 | 9014-01-1 |
| | Protex ® 30L; Protex 89L (G) | *Bacillus subtilis* | Subtilisin | 3.4.21.62 | 232-752-2 | 9014-01-1 |
| | Protex ® 40L (G) | *Bacillus subtilis* | Subtilisin | 3.4.21.62 | 231-752-2 | 9014-01-1 |
| | | *Tritirachium album* | Proteinase K | 3.4.21.62 | | |
| | | Porcine origin | Trypsin | 3.4.4.4 | 232-650-8 | 9002-07-7 |
| | | Bovine origin | Alpha-Chymotrypsin | 3.4.21.1 | 232-671-2 | 9004-07-3 |
| | | *Staphylococcus aureus* | Endoproteinase Glu-C | 3.4.21.19 | | |
| | | *Lysobacter enzymogenes* | Endoproteinase Lys-C | 3.4.21.50 | | |
| Thiol Protease | | Pineapple | Bromelain | 3.4.22.33 | 232-572-4 | 9001-00-7 |
| | | *Carica papaya* (Papaya) | Papain | 3.4.4.10 | 232-627-2 | 9001-73-4 |
| | | Latex from fig tree | Ficin | 3.4.4.12 | 232-599-1 | 9001-33-6 |

TABLE 1-continued

| Functional Class | Exemplary Protease Tradename | Origin, Natural Source | Recommended name (IUPAC) | Enzyme Classification # (IUPAC) | EINECS # | CAS # |
|---|---|---|---|---|---|---|
| Aspartyl Protease | CHY-MAX ® (CH) | bovine origin | Chymosin | 3.4.23.4 | | |
| | CHY-MAX ® M (CH) | bovine origin | Chymosin | 3.4.23.4 | | |
| | Thermolase ® (CH) | *Cryphonectria parasitica* | Endothiapepsin | 3.4.23.22 | | |
| | | *Mucor miehei* | Mucorpepsin/Rennin | 3.4.23.23 | | |
| | | Porcine origin | Pepsin | 3.4.23.1 | 232-629-3 | 9001-75-6 |
| | Protex ® 15L (G) | *Trichoderma reesei* | Aspergillopepsin | 3.4.23.18 | 232-796-2 | 9025-49-4 |
| | Protex ® 26L (G) | *Aspergillus niger* | Aspergillopepsin | 3.4.23.18 | 232-796-2 | 9025-49-4 |
| | Protex ®50FP; Protex ® 51FP (G) | *Aspergillus oryzae* var. | Aspergillopepsin | 3.4.23.18 | 232-796-2 | 9025-49-4 |
| Zinc Metalloprotease | | *Bacillus thermoproteolyticus rokko* | Thermolysin | 3.4.24.27 | 232-973-4 | 9073-78-2 |
| | Protex ®14L(G) | *Geobacillus* sp. | Thermolysin | 3.4.24.27 | 232-973-4 | 9073-78-3 |
| | | *Flavobacterium menigosepticum* | Endoproteinase Asp-N | 3.4.24.33 | | |

(G) = Dupont Industrial Bioscience (formerly Genencor),
(NZ) = Novozymes,
(CH) = Christian Hansen A/S In certain embodiments, the protease, or combination of proteases, in the formulation reduces Fel d 1 binding to anti-Fel d 1 antibodies by at least 50% under conditions applicable to the protease or combination thereof, as described in the Examples, as measured by one or more of ELISA, SDS-PAGE, or any other known method for detecting the presence of the antigen and/or antigenic epitopes or the binding of the antigen to Fel d 1-specific antibodies. For instance, the proteases can include one or more of subtilisin, proteinase K, alpha-chymotrypsin, trypsin, endoproteinase Lys-C, bromelain, papain, ficin, chymosin, endothiapepsin, mucorpepsin/rennin, pepsin, aspergillopepsin, thermolysin and endoproteinase Asp-N.

More particularly, the protease, or combination of proteases, in the formulation reduces Fel d 1 binding to anti-Fel d 1 antibodies by at least 90% under conditions applicable to the protease or combination thereof, as described in the Examples, as measured by one or more of ELISA, SDS-PAGE, or any other known method for detecting the presence of the antigen and/or antigenic epitopes or the binding of the antigen to Fel d 1-specific antibodies. For instance, the proteases can include one or more of subtilisin (e.g., from *Bacillus licheniformis, B. clausii, B. lentus B. amyloliquefaciens* and/or *B. subtilis*), trypsin (e.g., porcine), alpha-chymotrypsin (e.g., bovine), bromelain, papain, ficin, chymosin (e.g., bovine), endothiapepsin, mucorpepsin/rennin, pepsin, aspergillopepsin (e.g., from *Trichoderma reesei, Aspergillus niger* or *Aspergillus oryzae*), thermolysin and endoproteinase Asp-N.

In certain embodiments, the proteases include one or more of papain, subtilisin from *B. licheniformis*, aspergillopepsin from *A. oryzae*, endoproteinase Asp-N, bromelain, ficin, alpha-chymotrypsin, endothiapepsin from *Cryphonectria parasitica*, pepsin and thermolysin from *Geobacillus* sp. In particular embodiments, the proteases include one or more of papain, subtilisin from *B. licheniformis*, aspergillopepsin from *A. oryzae* and endoproteinase Asp-N.

The inventors have determined that certain proteases may be particularly suitable for use in compositions containing alcohol or certain detergents. For instance, in certain embodiments, the protease, or combination of proteases, reduces Fel d 1 binding to anti-Fel d 1 antibodies by at least 50% in the presence of up to 7.5% isopropanol under reaction conditions as set forth for the respective classes of enzymes in Table 2. These proteases can include one or more of ficin, bromelain, papain, aspergillopepsin from *Aspergillus oryzae*, or endoproteinase Asp-N. In other embodiments, the protease, or combination of proteases, reduces Fel d 1 binding to anti-Fel d 1 antibodies by at least 50% in the presence of non-ionic detergent, e.g., polysorbate 20 (Tween® 20) at up to 10%, under reaction conditions as set forth in Table 2. These proteases can include one or more of aspergillopepsin from *A. oryzae*, endoproteinase Asp-N, subtilisin from *B. licheniformis*, papain, bromelain and ficin. I was thinking the range should be broader?

The formulation can further comprise an additive that enhances the efficiency of the enzyme in degrading the Fel d 1. In certain embodiments, the additive is cysteine or calcium salts/ions ($Ca^{2+}$), or a combination of cysteine and calcium salts/ions, or compounds that form cysteine or calcium salts/ions in situ.

In various embodiments, the formulation is disposed within a composition selected from, for example: liquid, solid or powder cleaning agent, spray, moist cloth, wipe, sponge, water-dissolvable tablet, filter, food, oil or water supplement, vacuum cleaner filter or additive, granule, detergent, carpet and room deodorizer, litter, litter additive, mitt, additive for non-woven products, washing machine pod (tablet), multi chamber liquid tablets. Additionally, the formulations can be disposed of in an oral preparation. In one aspect, the formulation can be disposed within a toy, e.g. cat toy, including edible and non-edible toys.

In certain embodiments, the formulation can comprise a granule, powder or tablet that is reconstituted with a liquid (e.g., water, buffer or other liquid) prior to use. In other embodiments, the formulation can comprise a liquid or spray that can be applied to a surface or on the animal. Preferably, the spray does not aerosolize. Suitable sprays that do not aerosolize can be made in accordance with methods known in the art.

In certain embodiments, the formulations contain enzymes that are generally recognized as safe for use in foods and cosmetics. Such formulations are particularly suitable for use in soaps, shampoos, foams/mousses, powders, sprays, conditioners, rinses, gels, lotions, collars, dispersants, moist mitts, wipes, dentifrices and/or mouthwashes, or any other compositions suitable for applying to the skin, hair, fur or oral cavity, or disposed within an edible composition, or formulated for adding to any such compositions.

In certain embodiments, the protease has substantially no interaction with substances that include keratin, collagen, elastin, fibronectin, other proteins and fibers or fabric (in clothing, carpet, upholstery, curtains and bedding). Suitable proteases that are inactive on such proteins include, but are not limited to papain and pepsin.

In other embodiments, the protease may be active against keratin and may be useful in reducing keratin buildup that can occur when the pet is shampooed. For example, bromelain, ficin, aspergillopepsin, endothiapepsin, certain subtilisins, thermolysin, endoproteinase Asp-N and alpha-chymotrypsin were found to degrade keratin (Example 2).

Another aspect of the invention features a method of making a formulation for reducing or eliminating allergenicity of Fel d 1. In general, the method comprises combining at least one protease that interacts with the Fel d 1 and substantially degrades allergenic epitopes on the Fel d 1 with a medium in which the protease is active or can be made active prior to use. The medium can be any medium that satisfies the aforementioned requirement, including but not limited to liquids, solids, granules, powders, moist cloths, wipes, mitts, sponges, water-dissolvable tablets, filters, foods, dietary supplements, beverages, concentrates to add to foods and beverages, vacuum cleaner filters or additives, detergents, carpet, upholstery and room deodorizers, litters, litter additives, mitts, washing machine pods (tablet), to name just a few.

The proteases can include any of the proteases discussed hereinabove, or any combination thereof, in an amount suitable to degrade the Fel d 1 sufficiently to inhibit it from binding to anti-Fel d 1 antibodies during the time the formulation is exposed to the Fel d 1 in the environment (around the cat, on the cat or in the cat). For instance, formulations intended to be applied to an environment and removed shortly thereafter (e.g., within minutes or hours), such as a cleaning agent, pet shampoo or oral product, should contain a concentration of protease(s) sufficient to degrade Fel d 1 within that time period. The kinetic analyses discussed in the Examples provide concentration ranges of the proteases to achieve such a result. For example, kinetic analysis of papain and subtilisin from $B.$ $licheniformis$ in artificial cat saliva revealed that, under normal cat saliva conditions, more than 80% of Fel d 1 was degraded within 5 minutes by papain at 4.5 mg ml$^{-1}$ and by the subtilisin at 9.5 mg ml$^{-1}$. Formulations intended to remain in place for an extended time (e.g., several hours or overnight), such as an upholstery or fabric spray or a leave-in mousse, gel, shampoo or spray, would require a lesser concentration of protease(s).

The skilled artisan can measure Fel d 1 degradation by any method known in the art. For example, degradation of Fel d 1 can be measured by ELISA and/or SDS-PAGE, or combinations thereof. In a particular embodiment, ELISA assays are used to determine the amount of binding of Fel d 1 to Fel d 1-specific antibodies following exposure to the protease(s).

In one embodiment, protease activity is measured and standardized using a standard protease assay. Using such an assay, protease activities can be standardized across proteases and assay conditions. A typical protease activity assay system includes a protease substrate and a suitable buffer to support protease activity, and may also include diluents or solvents and other agents useful for the activity of proteases (e.g., cysteine). Typically, the substrate is designed such that cleavage of the substrate by the protease generates a detectable product. For instance, one type of protease assay utilizes a protein, e.g., casein, derivatized to contain fluorophore that is quenched until the protease cleaves the protein. Upon cleavage by the protease, the fluorophore is separated from the quencher and yields a quantitatively detectable fluorescence signal.

Other types of protease activity assays are also suitable for use. For instance, an assay may utilize a succinylated protein, such as casein, as a substrate. Hydrolysis of this substrate in the presence of protease results in the release of peptide fragments with free terminal amino groups. These peptides are reacted with trinitrobenzene sulfonic acid (TNBS), followed by measurement of the absorbance increase that results from the formation of yellow colored TNB-peptide adducts.

The enzyme activities determined by a protease assay can be expressed generally as relative product units per second and normalized to the amount of enzyme preparation (rpu $s^{-1}$ $g^{-1}$). In the case of a fluorescence-based assay such as the one described above, the enzyme activities can be expressed as relative fluorescence units per second and normalized to the amount of enzyme preparation (rfu $s^{-1}g^{-1}$).

The method comprises combining the requisite amount of the protease with the medium. The amount of protease to include in the formulation will depend on whether it is prepared in "ready to use" form, or as a concentrate for later dilution.

Another aspect of the invention features a method of reducing or eliminating allergenic Fel d 1 from the environment. The method comprises contacting an element of the environment where Fel d 1 is present with a formulation comprising at least one protease that interacts with the Fel d 1 and substantially degrades allergenic epitopes on the Fel d 1, thereby reducing or eliminating allergenic Fel d 1 from the environment.

In certain embodiments, the environment is "around the cat." In one embodiment, the Fel d 1 is present on an inanimate surface and the formulation is applied to the surface. Typical surfaces can include counters, floors, walls, furniture, upholstery and clothing, to name a few. In another embodiment, the Fel d 1 is airborne and the formulation is contacted with the air. For instance, the formulation can be disposed within a filter through which air passes, such as an air filter for a fan, heater or air conditioner, or a vacuum cleaner filter.

In other embodiments, the environment is "on the cat." and the formulation is applied to the portion of the animal on which the Fel d 1 is present. For instance the Fel d 1 may be present on the hair, fur or external skin of the animal, or on saliva deposited on the hair, fur or skin of the animal. In other embodiments, the environment is "in the cat," typically in the mouth of the animal where Fel d 1—containing saliva is produced, and the formulation is applied as a dentifrice, rinse, food, treat, film or strip foam or spray or beverage.

Another aspect of the invention features an article of manufacture (also referred to herein as a "product") comprising a formulation that includes at least one protease that interacts with the Fel d 1 and substantially degrades allergenic epitopes on the Fel d 1, and instructions for its use in reducing or eliminating allergenic Fel dl from the environment. In one embodiment, the product can be formulated as a liquid, solid or powder cleaning agent, spray, moist cloth, wipe, sponge, water-dissolvable tablet, detergent, carpet or fabric deodorizer, litter, litter additive, mitt, additive for non-woven or woven products, washing machine pod (tablet), multicompartment liquid tablet, for application to an inanimate surface. In another embodiment, the product can be formulated as an air filter additive for contacting airborne Fel d 1.

In other embodiments, the product is formulated for application or administration to an animal that produces the Fel d 1. For instance, the product can be formulated as a shampoo, conditioner, rinse, mousse, gel, spray, lotion or powder for application to hair, fur or external skin of the animal. Alternatively, the product can be formulated as a dentifrice, food, treat, or additive to the animal's food or water, for application to the mouth of the animal.

Such products and articles of manufacture as disclosed herein can be effective for inactivating Fel d 1 in an environment. In one embodiment, the products and/or articles can reduce or inactivate Fel d 1 by at least 10% in their respective environments. In some aspects, Fel d 1 can be inactivated by the products and/or articles by at least 50%. In other aspects, Fel d 1 can be inactivated by at least 1%, 5%, 15%, 20%, 30%, 40%, 60%, 70%, 80%, 90%, or even by at least 95%.

In certain embodiments, the product comprises a food or other edible composition for reducing or eliminating the allergenicity of the cat allergen Fel d 1. In one embodiment, the food product is a dry pet food or pet treat comprising a protease-containing formulation. For example, the formulation can be applied by dusting or coating the formulation onto the dry food composition prior to packaging or shipping. Because the food product is dry, activity of the proteases can be preserved during shipping and storage. The formulation can also be provided as a concentrate that is dissolved prior to feeding, or a sachet or pouch containing a powdered or granular protease preparation that can be sprinkled onto a food composition or mixed into water or other liquid beverages. The formulation can be provided as a liquid formulation that can be applied, for example, directly to a food composition (dry, moist or intermediate), or to water or other liquid beverages.

In a further aspect, the present invention provides kits for reducing or eliminating the allergenicity of the cat allergen Fel d 1. In general, these kits comprise one of the aforementioned protease-containing formulations and instructions for their use in removing allergenic Fel d 1 from the environment.

In one embodiment, the kit comprises a composition for cleaning or otherwise removing Fel d 1 from the environment around the cat, such as a surface of an inanimate object. These include, for instance, a liquid, solid or powder cleaning agent, spray, moist cloth, wipe, sponge, carpet and room deodorizer, granule or detergent, said composition comprising the Fel d 1-degrading formulation, along with instructions for use. In certain embodiments, the protease formulations can be provided in concentrated form and the instructions will contain directions for dilution. In other embodiments, a multi-component kit is provided. For example, a cleaning kit can comprise a cleaning agent in one container and a protease formulation in another, and the instructions can direct the user on how to combine the components prior to use. Such embodiments can be particularly beneficial if the proteases in the formulation are sensitive to ingredients in the cleaning agent, such that they would be inactivated by the cleaning agent with prolonged exposure.

Likewise, the kit may comprise a composition for washing fabric, such as a liquid, solid or powder, water-dissolvable tablet or washing machine pod (tablet), said composition comprising the Fel d 1-degrading formulation, along with instructions for use. In another embodiment, the kit comprises an air filter, such as a vacuum cleaner filter or additive, comprising the Fel d 1-degrading formulation, along with instructions for use. In these embodiments, the protease formulations again can be provided in concentrated form and the instructions can contain directions for dilution. In other embodiments, a multi-component kit is provided. For example, a laundry kit can comprise a laundry detergent in one container and a protease formulation in another, and the instructions can direct the user on how to combine the components prior to use. An air filter kit can comprise the air filter and the protease formulation, and instructions for combining the two to reduce or eliminate airborne Fel d 1.

In another embodiment, the kit comprises treatments for "on the cat," e.g., fur, hair or skin. Such kits can include a soap, shampoo, powder, spray, conditioner, rinse, mousse, gel, lotion, collar, dispersant or moist mitt or wipe suitable for applying to the skin, hair or fur or formulated for adding to any such compositions, along with instructions for use. The protease-containing formulation can be included within the fur/hair treatment composition, or it can be provided separately, as a concentrate or otherwise, and mixed with the fur/hair treatment prior to use. The kits can also contain a combination of fur/hair treatments. For instance, a kit can comprise a mitt or cloth for wiping the fur and a liquid protease formulation. The instructions can provide directions on how to impregnate the mitt or cloth with the liquid and apply it to the cat. As another example, a kit can comprise a shampoo and a rinse, spray, gel or mousse wherein the shampoo is a standard pet shampoo that does not contain the protease formulation and the rinse, spray, gel or mousse contains the protease formulation.

In another embodiment, the kit comprises an oral composition, such as a liquid, solid or powder, moist cloth, wipe, dentifrice or mouthwash, said composition comprising the Fel d 1-degrading formulation, suitable for applying to the oral cavity, or formulated for adding to any such compositions, along with instructions for use. In another embodiment, the kit comprises a dental kit comprising a water-dissolvable tablet that can be administered to the animal, such as by dissolving in drinking water.

In another embodiment, the kit comprises an edible form of a composition described herein in a sachet or pouch attached to or recommended to be used alongside to a food composition, such as a pet food package, along with instructions for mixing the edible composition into the food, adding the composition to the food, or dissolving, mixing, or adding the composition to a fluid that is to be administered to the animal receiving the food, such as drinking water. In another embodiment, the kit comprises at least a food composition described herein comprising the Fel d 1-degrading formulation, along with instructions for use. In another kit, a concentrated form of the composition is provided, and also provided is a tool or device for conveniently measuring a suitable amount of the concentrate for mixing with, adding to, diluting, or dissolving with a food or fluid to be provided to the animal. In one kit, the composition in edible form is provided in a convenient dosage in a series of identical packages, such that one package of the composition is added to one package (e.g. can) of pet food without a requirement for measuring. Such kits can be provided such that for each package of pet food in a point-of-sale package, there is one package of Fel d 1-degrading formulation provided. For example, twelve cans of food and twelve packages of composition are packaged together in a single kit.

In any of the foregoing embodiments, the kit can comprise a composition, in concentrated or other form, instructions for use, including, if required, instructions for preparation of a suitable dilution, and optionally one or more of a diluent or extender, a tool or measuring device for preparing a suitable dilution, and an applicator such as a sprayer, duster, wipe, or the like. Such kits may be useful for compositions formulated for treating surfaces, for treating the air in an environment, or for treating an animal with a composition for external use.

For all such kits, the kits may include devices, applicators, dilutors, and the like that are automatic or the automate the dosing, dilution, mixing, addition, or application of the composition for an appropriate use. For any of the kits described herein, they can be provided as sachets or bundled with other products to maximize convenience, compliance, and efficiency of use and purchase. Thus, the kits can include, or be bundled with any or all of food for the pet, bedding for pet, shampoo or cosmetic items for the pet, medicine for the pet.

Any of the foregoing kits, as well as others can also be provided as virtual kits. When the kit comprises a virtual package, the kit provides instructions in a virtual environment in combination with one or more physical kit components, such as those described above. The kit contains at least one composition described herein, and other components, including optional components. The kits may contain the kit components in any of various combinations and/or mixtures. In one embodiment, the kit contains a packet containing one or more compositions and a container of food for consumption by an animal. The kit may contain additional items such as a device for mixing the compositions and ingredients or a device for containing the admixture, e.g., a food bowl. In another embodiment, the compositions are mixed with additional nutritional supplements such as vitamins and minerals that promote good health in an animal. Further information and instructions are provided in the virtual environment that is provided to the purchaser—i.e. directions to a website, faxback server, or an included computer readable device such as a CD-ROM and/or an application ("app") for a device.

In another aspect, the invention provides a communication means, or a means for communicating information about or instructions for one or more of the formulations, methods, compositions, articles of manufacture, products and/or kits described herein for reducing the allergenicity of, or the amount of allergenic Fel d 1 from the environment. In various embodiments, the information pertains to formulations, compositions, articles of manufacture or products of the present invention. In other embodiments, the information pertains to methods or kits useful for practicing the invention described herein. In other embodiments, the information relates to combinations of any of the foregoing.

The communication means comprises one or more of text information, audio information, still or moving images, including animations, or video. In various embodiments, the communication means comprises one or more of a printed document, a static or dynamic electronic document, for example a hypertext document, a computer readable or digital storage medium, including but not limited to electronic, optical, or magnetic media of any type, audio information, an audio, audiovisual or visual display or presentation, or video information however encoded, wherein the communication means displays or contains information or instructions comprising any of the aforesaid. In certain embodiments, the communication means comprises a web site, an FAQ (Frequently Asked Questions) page or file, an electronic file or collection of two or more electronic files of the same or different types, an email or email file, a visual display, kiosk, brochure, advertisement, package or product label, package or product insert, handout, public announcement, audiotape or electronic audio file embodied in any machine-readable or computer-readable medium, a videotape, videodisk, or electronic video file embodied in any machine readable or computer-readable medium, DVD, CD-ROM, app, or the like, or any combination of the foregoing containing such information or instructions. Useful information includes one or more of (1) methods and techniques for combining and administering the allergen-specific molecules and/or other components, (2) contact information for allergic animals or their guardians or caregivers to use if they have a question about the kit, the composition, or its use; (3) nutritional information about food compositions, and other components provided in any kit, (4) safety information including for example emergency information, and further contacts in the event of adverse reaction; poison control, material data safety sheets, (5) information useful for reordering, for example through automatic fulfillment systems; (6) general information about allergies, environmental allergens, and methods for minimizing or eliminating specific environmental allergens. Useful instructions can include amounts for mixing and administration amounts and frequency. The communication means is useful for instructing on the benefits of using the present invention and communicating the approved methods for administering the invention to an animal.

Another aspect of the invention provides a package comprising any one or more of the formulations, compositions, products and/or kits described herein. The package has affixed thereto a label containing a word or words, picture, symbol, design, acronym, slogan, phrase, or other device, or combination thereof (the label "device"), that indicates that the contents of the package contains a protease formulation for reducing or eliminating allergenic Fel d 1 from the environment.

EXAMPLES

Various aspects of the invention can be further illustrated by the following examples. It will be understood that these examples are provided merely for purposes of illustration and do not limit the scope of the invention disclosed herein unless otherwise specifically indicated.

Example 1

A set of 32 proteases, in combination with chemical agents such as cysteine, were tested for their ability to degrade Fel d 1. While not intending to be limited to a particular mechanism, the rationale for enzyme-catalyzed inactivation of Fel d 1 was to determine which proteases could degrade Fel d 1 such that IgE antibodies would not be able to recognize and bind to Fel d 1, resulting in the failure to mount an immune response and allergic reaction. Candidate proteases were selected from several different families of proteases, including serine proteases, thiol proteases, aspartic acid proteases and zinc metalloproteases.

To standardize activities and identify optimal reaction conditions for each candidate protease, the ENZCHEK® Protease Assay Kit (green fluorescence) from Invitrogen, Inc. (Carlsbad Calif.) was used, which is based on casein as substrate, derivatized to contain fluorophore that is quenched until cleaving by the protease. The enzyme activities determined by the protease assay were expressed as relative fluorescence units per second and normalized to the amount of enzyme preparation (rfu s$^{-1}$ g$^{-1}$). To identify appropriate reaction conditions for the different classes of enzymes, different buffers and pH conditions were tested at 37° C. Table 2 provides the pH of the buffer with the best performance, and the activity (increase of fluorescence per second, rfu s$^{-1}$) per amount of protease preparation (g$^{-1}$) as determined by the ENZCHEK® Protease Assay.

Most of the proteases tested (serine proteases, thiol proteases and zinc-metalloproteinases) showed optimal activity in reaction buffers at pH 7.8. The aspartic acid proteases were optimally active at pH 4.0 or pH 6.0. Some serine and aspartic acid proteases were activated by the addition of calcium salt/ions (Ca$^{2+}$). The thiol proteases were significantly more active when cysteine was added to the reaction buffer. Endoproteinase Lys-C was the only protease that was not active in the ENZCHEK® Protease Assay under the tested conditions.

To characterize Fel d 1 degradation, different concentrations of candidate proteases were incubated with Fel d 1 at 37° C. overnight (~18 hours), followed by separation of proteins by gel electrophoresis (SDS-PAGE under non-reducing conditions) and COOMASSIE® staining. A typical reaction mix to test Fel d 1 degradation contained 2.5 µg of natural Fel d 1 (nFel d 1, LOTOX® Natural Feld d 1 was obtained from Indoor Biotechnologies (LTN-FD1-1)) and varying concentrations of candidate proteases in a total reaction volume of 20 µl (final Fel d 1 concentration of 125 µg ml$^{-1}$). Fel d 1 has been reported to be a 35 kDa tetrameric glycoprotein formed by two heterodimers of 18 kDa. Therefore, Fel d 1 degradation was assessed by the extent of disappearance of the Fel d 1 protein band at approximately 18 kDa. For most proteases, conditions were optimized to promote complete degradation of Fel d 1 with minimal protease activity. For all tested proteases, the minimal activity (rfu s$^{-1}$) as well as the corresponding amount of enzyme (µg) that was required to completely degrade 2.5 µg Fel d 1 in 20 µl of buffer (with optimal pH for the respective protease) was estimated based on the absence of the Fel d 1 band on the SDS-PAGE gel. The results are summarized in Table 2.

TABLE 2

Characterization and activity of proteases

| Name or trade name | Description/Source[a] | Activity Manufacturer[b] | EnzChek®[c] [rfu s$^{-1}$ g$^{-1}$] | Opt. pH[d] | Min. req. [rfu s$^{-1}$] | activity[e] [µg] |
|---|---|---|---|---|---|---|
| Serine proteases | | | | | | |
| Alcalase® 2.4L | Subtilisin *B. licheniformis* | ≥2.4 U g$^{-1}$ | 2.39 * 10$^7$ | pH 7.8 | 1-10 | 0.04-0.42 |
| Savinase® 16.0L | Subtilisin *Bacillus* sp. | ≥16 U g$^{-1}$ | 5.34 * 10$^8$ | pH 7.8 | ~100 | ~0.19 |
| Everlase® 16.0L | Subtilisin *Bacillus* sp. | ≥16 U g$^{-1}$ | 9.92 * 10$^7$ | pH 7.8 | 100-1000 | 1.0-10 |
| Esperase® 8.0L | Subtilisin from *Bacillus* sp. | ≥8 U g$^{-1}$ | 1.08 * 10$^9$ | pH 7.8 | ~1000 | ~0.93 |
| Purafect® | Subtilisin | n.a. | 2.40 * 10$^8$ | pH 7.8 | >100 | >0.42 |
| Protex® 6L | Subtilisin *B. licheniformis* | 7670 U g$^{-1}$ | 5.33 * 10$^8$ | pH 7.8 | 10-100 | 0.02-0.19 |
| Protex® 7L | Subtilisin *B. amyloliquefaciens* | 265 U g$^{-1}$ | 1.51 * 10$^5$ | pH 7.8 | <1 | <6.6 |
| Protex® 8L | Subtilisin *B. licheniformis* | 4760 U g$^{-1}$ | 4.44 * 10$^8$ | pH 7.8 | ~100 | ~0.22 |
| Protex® 30L | Subtilisin *B. subtilis* | 1745 U g$^{-1}$ | 2.01 * 10$^7$ | pH 7.8 | 10-100 | 0.50-5.0 |
| Protex® 40L | Subtilisin *B. subtilis* | 3625 U g$^{-1}$ | 4.97 * 10$^8$ | pH 7.8 | ~100 | ~0.20 |
| Protex® 89L | Subtilisin *B. subtilis* | 1930 U g$^{-1}$ | 1.53 * 10$^7$ | pH 7.8 | 10-100 | 0.65-6.5 |
| BLAP (Henkel) | Subtilisin *B. lentus* | n.a. | 2.40 * 10$^8$ | pH 7.8 | >100 | >0.42 |
| Proteinase K | Subtilisin *Tritirachium album* | 38.4 U g$^{-1}$ | 3.22 * 10$^7$ | pH 7.8 | ~1000 | ~31 |
| Trypsin | porcine pancreas | 1-2 MU g$^{-1}$ | 1.95 * 10$^7$ | pH 7.8 Ca | 10-100 | 0.51-5.1 |
| α-Chymotrypsin | porcine pancreas | ≥40 kU g$^{-1}$ | 2.35 * 10$^8$ | pH 7.8 Ca | 10-100 | 0.04-0.42 |
| Endoproteinase Glu-C | V8 protease *S. aureus* | ~760 kU g$^{-1}$ | 5.95 * 10$^6$ | pH 7.8 | not active | (>16 µg) |
| Endoproteinase Lys-C | *Lysobacter enzymogenes* | n.a. | not active | | not active | (>0.5 µg) |
| Thiol proteases | | | | | | |
| Bromelain | pineapple | 500 U g$^{-1}$ | 7.35 * 10$^8$ | pH 7.8 Cys | 270-2700 | 0.37-3.7 |
| Papain | papaya | >3 * 10$^7$ U g$^{-1}$ | 6.40 * 10$^8$ | pH 7.8 Cys | ~60 | ~0.093 |
| Ficin | fig tree latex | 200 U g$^{-1}$ | 1.69 * 10$^9$ | pH 7.8 Cys | 460-4600 | 0.28-2.8 |
| Aspartic acid proteases | | | | | | |
| CHY-MAX® | Chymosin | n.a. | 1.58 * 10$^4$ | pH 4.0 Ca | >10 | >630 |
| CHY-MAX® | Chymosin | n.a. | 3.96 * 10$^3$ | pH 4.0 | not active | (>2.5 mg) |
| Thermolase® | Chymosin *C. parasitica* | n.a. | 1.59 * 10$^6$ | pH 4.0 Ca | ~10 | ~6.3 |
| Mucorpepsin | Chymosin *Mucor miehei* | 120 U g$^{-1}$ | 4.07 * 10$^6$ | pH 4.04.07-41 | 1.0-10 | |
| Pepsin | porcine pancreas | 800 U g$^{-1}$ | 2.55 * 10$^6$ | pH 4.02.55-26 | 1.0-10 | |
| Protex® 15L | *Trichoderma reesei* | 31 U g$^{-1}$ | 3.40 * 10$^6$ | pH 4.0~10 | 2.9 | |
| Protex® 26L | *Aspergillus niger* | 190 U g$^{-1}$ | 5.94 * 10$^6$ | pH 4.0~10 | 1.7 | |
| Protex® 50FP | *Aspergillus oryzae* var. | 105 U g$^{-1}$ | 2.39 * 10$^6$ | pH 4.0~1 | 0.42 | |
| Protex® 51FP | *Aspergillus oryzae* var. | 1355 U g$^{-1}$ | 2.21 * 10$^7$ | pH 6.0~100 | 4.5 | |

TABLE 2-continued

Characterization and activity of proteases

| Name or trade name | Description/Source[a] | Activity Manufacturer[b] | EnzChek ®[c] [rfu s$^{-1}$ g$^{-1}$] | Opt. pH[d] | Min. req. [rfu s$^{-1}$] | activity[e] [µg] |
|---|---|---|---|---|---|---|
| Zinc-metalloproteases | | | | | | |
| Thermolysin | B. thermoproteolyticus rokko | 50-100 kU g$^{-1}$ | 2.13 * 10$^8$ | pH 7.8 | not active | (>4.7 µg) |
| Protex ® 14L (Gr) | Thermolysin Geobacillus sp. | 38 U g$^{-1}$ | 2.92 * 10$^6$ | pH 7.8 | ~500 | ~171 |
| Endoproteinase Asp-N | Flavastacin | 25 kU g$^{-1}$ | 2.24 * 10$^7$ | pH 7.8[f] | ~50 | 2.2 |

[a]Name of abbr. organisms: Bacillus licheniformis, Bacillus amyloliquefaciens, Bacillus lentus, Staphylococcus aureus, Cryphonectria parasitica, Bacillus thermoproteolyticus rokko
[b]Activity of the protease lot as indicated on the datasheet of the manufacturer. Activities (in U g$^{-1}$) are determined by variable methods and thus can not be directly compared
[c]Activity (increase of fluorescence per second, rfu s$^{-1}$) per amount of protease preparation (g$^{-1}$) as determined by the EnzChek ® protease assay (Invitrogen, E6638)
[d]pH of the reaction buffer at which highest activities were determined by the EnzChek ® protease assay. Ca, addition of calcium. Cys, addition of cysteine
[e]Minimal activity (as determined in the EnzChek ® protease assay (in rfu s$^{-1}$) and the corresponding amount of protease preparation (in µg) that is required to completely degrade 2.5 µg of natural Fel d 1 in 20 µl reaction mix as determined by SDS-PAGE (see text for details).
[f]The buffer that was supplemented by the manufacturer was used for the EnzChek ® protease assay as well as Fel d 1 degradation Various serine proteases candidates were tested for their ability to degrade Fel d 1. For example, the Fel d 1 proteolytic activity of a subtilisin from B. licheniformis (bl) (ALCALASE® 2.4 L, Novozymes A/S Bagsvaerd, Denmark) was determined. Natural Fel d 1 (1.9 µg) was incubated with 0.1, 1 or 10 rfu s$^{-1}$ of the bl subtilisin overnight at 37° C. in 20 µl of either Tris/HCl buffer (200 mM, pH 7.8) or ammonium acetate buffer (100 mM, pH 4.0). The subtilisin (10 rfu s$^{-1}$) without Fel d 1 and Fel d 1 without the subtilisin served as controls. Fel d 1 was completely degraded by 10 rfu s$^{-1}$ of the bl subtilisin in Tris/HCl buffer, but not in ammonium acetate buffer conditions as determined by SDS-PAGE and COOMASSIE® staining (FIG. 1). These experiments revealed that the minimum amount of bl subtilisin required to completely degrade 1.9 µg Fel d 1 in 20 µl Tris/HCl buffer is 1-10 rfu s$^{-1}$ (0.04-0.42 µg).

Subtilisins from B. clausii (bc) (SAVINASE® 16.0 L, EVERLASE® 16.0 L, Novozymes) and B. halodurans (bh) (ESPERASE® 8.0 L, Novozymes) were also assessed to determine the minimum amount of protease required to degrade Fel d 1. In these experiments, natural Fel d 1 (2.5 µg) was incubated with 100 or 1000 rfu s$^{-1}$ of the respective subtilisin overnight at 37° C. in 20 µl sodium phosphate buffer (100 mM, pH 7.8). Protease (1000 rfu s$^{-1}$) without Fel d 1 and Fel d 1 without protease served as controls. The minimum amounts of the respective proteases required for degradation of 2.5 µg Fel d 1 in 20 µl are shown in Table 2.

The vegetable thiol proteases bromelain, papain and ficin from the edible plants pineapple, papaya and fig tree, respectively, were assayed for degradation of Fel d 1. For the SDS-PAGE experiments, natural Fel d 1 (2.5 µg) was incubated overnight at 37° C. with different amounts of papain, bromelain or ficin in sodium phosphate buffer (100 mM, pH 7.8) containing 40 mM cysteine. Buffer with cysteine alone, enzyme without Fel d 1 in cysteine-free buffer and Fel d 1 without enzyme (with and without cysteine) served as controls. The thiol proteases bromelain, papain and ficin were all able to completely degrade Fel d 1 as determined by SDS-PAGE and COOMASSIE® staining. As shown in Table 2, the optimal conditions for bromelain, papain and ficin determined by the ENZCHEK® Protease Assay include a pH of 7.8 in the presence of cysteine. Specifically, the addition of 40 mM cysteine increased the activities of each of bromelain, papain and ficin by factors of 270, 60 and 460, respectively, as determined by the ENZCHEK® Protease Assay. Table 2 shows the minimum amounts of these proteases required for degradation of 2.5 µg Fel d 1 in 20 µl cysteine-containing buffer.

In addition, the aspartic acid proteases endothiapepsin from Cryphonectria parasitica (THERMOLASE®, Chr. Hansen, Hørsholm, Denmark) and chymosin of bovine origin (CHY-MAX®, Chr. Hansen, Hørsholm, Denmark) were both optimally active at pH 4.0 in the presence of calcium salt/ions (Ca$^{2+}$) (Table 2). Natural Fel d 1 (2.5 µg) was incubated overnight at 37° C. with 0.1, 1 or 10 rfu s$^{-1}$ of the proteases in 20 µl of ammonium acetate buffer (100 mM, pH 4.0) containing 10 mM calcium chloride. Buffer without Fel d 1 and Fel d 1 without enzyme served as controls in this experiment. Table 2 shows the minimally required protease amounts for degradation of 2.5 µg Fel d 1 in 20 µl buffer for the two aspartic acid proteases.

Some of the candidate proteases were tested for their abilities to degrade 2.5 µg of natural Fel d 1 in 20 µl optimal reaction buffer at 37° C. within short incubation time points by adding a protease inhibitor after one or two hours to stop the reaction. Reactions were visualized by SDS-PAGE followed by COOMASSIE® staining. It was found that 50 rfu s$^{-1}$ (2.1 µg) of a bl subtilisin (ALCALASE® 2.4 L) was sufficient to completely degrade Fel d 1 within one hour of incubation when using 1 mM phenylmethylsulfonyl fluoride (PMSF) as inhibitor. Moreover, 600 rfu s$^{-1}$ (0.93 µg) of papain degraded most Fel d 1 after one hour of incubation when using 10 µM E64 as inhibitor. 500 rfu s$^{-1}$ (171 µg) of thermolysin from Geobacillus sp. (PROTEX® 14 L, DuPont Industrial Biosciences) was sufficient to completely degrade 2.5 µg Fel d 1 following overnight incubation, but only partial degradation occurred after two hours incubation when using 10 mM ethylenediaminetetraacetic acid (EDTA) as inhibitor. The kinetic studies using protease inhibitors revealed that complete Fel d 1 degradation generally could be achieved in a shorter time by increasing the protease concentration. Likewise, greater amounts of Fel d 1 could be degraded by increasing the protease concentration.

To summarize, the results from the Fel d 1 proteolysis experiments using the panel of 32 protease candidates revealed that proteases from all classes were able to completely degrade Fel d 1. As shown in Table 2, the candidate proteases exhibited varying degrees of Fel d 1 degradation activities. Most candidate proteases were capable of degrading 2.5 µg Fel d 1 in 20 µl at an activity less than 100 rfu s$^{-1}$.

Figure 2:
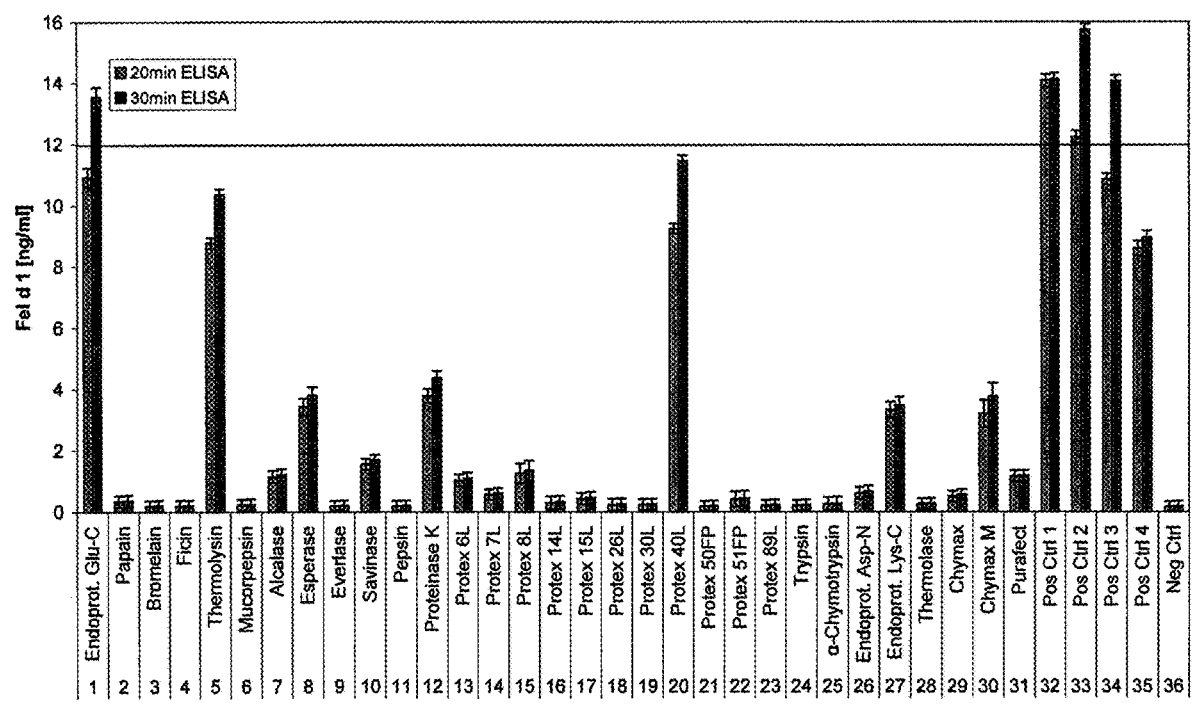
FIG. 2. Histogram showing residual Fel d 1 concentration after protease-catalyzed degradation as determined by ELISA. Natural Fel d 1 (2.5 µg) was incubated overnight with all tested commercial proteases (except for BLAP) in 20 µl of the optimal buffer at minimally required activities to achieve complete degradation of Fel d 1 (c.f. Table 2). The samples were diluted and analyzed by ELISA with time intervals of 20 and 30 minutes. As a result of the dilution, an initial concentration of 12 ng ml$^{-1}$ of Fel d 1 was expected (i.e. in the absence of degradation). The negative control (Neg Ctrl) contained no Fel d 1, the positive controls contained Fel d 1 incubated with the different buffers: Pos Ctrl 1: Tris/HCl buffer (200 mM, pH 7.8), Pos Ctrl 2: sodium phosphate buffer (100 mM, pH 7.8), Pos Ctrl 3: sodium phosphate buffer (100 mM, pH 6.0), Pos Ctrl 4: ammonium acetate buffer (100 mM, pH 4.0). Protease-catalyzed degradations were performed in duplicates.

Next, the ability of Fel d 1 specific antibodies to recognize and bind Fel d 1 after proteolysis was determined by ELISA. Natural Fel d 1 and Fel d 1 specific antibodies were obtained from Indoor Biotechnologies Ltd (Indoor Biotechnologies Ltd (Cardiff, Wales). ELISA conditions were determined such that a reliable quantitation of natural Fel d 1 in a range of concentrations from 0.3 to 12 ng ml$^{-1}$ was possible. Various candidate proteases, as indicated in FIG. 2, were incubated with Fel d 1 (2.5 μg) overnight in 20 μl of the optimal buffer at minimally required activities to achieve complete degradation of Fel d 1 (See optimized conditions reported in Table 2). Samples were diluted to a final theoretical Fel d 1 concentration of 12 ng ml$^{-1}$ (initial substrate concentration) and analyzed by ELISA at two different assay reading time points (20 and 30 minutes). After incubating Fel d 1 with a candidate protease, plates coated with anti-Fel d 1 antibody were used to capture Fel d 1. Then, an enzyme-linked detecting antibody that binds Fel d 1 was added, followed by the addition of substrate, which was enzymatically converted to a detectable signal. In the event that the proteases degrade Fel d 1, such that Fel d 1 epitopes required for binding to anti-Fel d 1 antibody are no longer present and/or accessible, the anti-Fel d 1 antibodies would not bind Fel d 1 and no signal would be detected by ELISA. As a control to verify that protease activity was not interfering with the ELISA assay, the ELISA was repeated but with the addition of a defined amount of Fel d 1. SDS-PAGE experiments as described above were conducted on all tested proteases to confirm Fel d 1 degradation and ELISA results.

Results are shown in FIG. 2. As can be seen, complete suppression of Fel d 1 binding to Fel d 1-specific antibodies was achieved with several of the subtilisin serine proteases, as well as trypsin and alpha-chymotrypsin; the thiol proteases degraded Fel d 1. Taken together, the ELISA and SDS-PAGE experiments demonstrate that antibody binding correlates with Fel d 1 degradation. For all tested proteases, the degree of Fel d 1 degradation, as estimated by SDS-PAGE, corresponded to the residual Fel d 1 concentration, as determined by ELISA. While not intending to be limited to a particular mechanism, these results suggest that the Fel d 1 degradation products no longer contain epitopes that bind to the Fel d 1 specific antibodies, and that protease-catalyzed degradation of Fel d 1 results in the suppression of Fel d 1 binding to epitope-specific Fel d 1 antibodies. Therefore, it is expected that Fel d 1 degradation by proteases can suppress IgE mediated allergic reactions. Most of the tested proteases were able to completely degrade Fel d 1 and suppress the binding of the resultant degradation products to epitope specific antibodies. Representative proteases from these experiments capable of completely degrading Fel d 1 (referred to below as "hit" proteases) include papain, subtilisin from *B. licheniformis* (bl subtilisin, PROTEX® 6 L), aspergillopepsin from *A. oryzae* (ao aspergillopepsin, PROTEX® 50 FP), endoproteinase Asp-N, bromelain, ficin, alpha-chymotrypsin, endothiapepsin from *Cryphonectria parasitica* (cp endothiapepsin, THERMOLASE®), pepsin and thermolysin from *Geobacillus* sp. (PROTEX® 14 L). Table 3 summarizes the properties of these "hit" proteases, with details provided in the following Examples.

TABLE 3

Summary of properties of "hit" proteases[a]

| | Keratin hydrolysis[b] | | Vitality of keratinocytes[c] | | Cellulose hydrol[d] | Protease inactivation, LD$_{50}$[e] | |
| --- | --- | --- | --- | --- | --- | --- | --- |
| | | TNBS | | | Cellulose azure | | Tween |
| Name/trade name/type | Keratin azura | Abs. 405 nm | WST-1 | Sulforhodamin B | Abs. 575 nm | Isopropanol | 20 ® |
| Group 1 hit proteases | | | | | | | |
| Papain (thiol) | 9.0% ± 7.4% | 0 ± 0.01 | 103.4% ± 19.9% | 99.1% ± 2.4% | 0.00 ± 0.01 | 10.0%-12.5% | 10%-20% |
| Protex ® 6L (serine) | 34.0% ± 33.5% | 0.32 ± 0.02 | 110.5% ± 40.1% | 107.5% ± 3.3% | 0.00 ± 0.01 | 2.5%-5.0% | >30% |
| Protex ® 50FP (aspartyl) | 0.0% ± 0.1% | 0.36 ± 0.06 | 92.8% ± 17.8% | 108.2% ± 2.0% | 0.08 ± 0.00 | 7.5%-10.0% | >30% |
| Endoproteinase Asp-N (metallo) | 0.43%[f] | 0.68 ± 0.03 | 24.7% ± 4.6% | 3.7% ± 3.0% | n.d.[g] | 7.5%-10.0% | >30% |
| Group 2 hit proteases | | | | | | | |
| Bromelain (thiol) | 43.2% ± 23.3% | 0.28 ± 0.02 | 25.6% ± 5.2% | 6.7% ± 1.4% | 0.00 ± 0.02 | >25% | 20%-30% |
| Ficin (thiol) | 33.1% ± 8.5% | 0.21 ± 0.02 | 23.3% ± 4.0% | 6.7% ± 0.5% | 0.00 ± 0.03 | >25% | 20%-30% |
| Pepsin (aspartyl) | 0.1% ± 0.6% | 0 ± 0.04 | 92.4% ± 19.6% | 100.9% ± 3.5% | 0.01 ± 0.01 | 5.0%-7.5% | n.d.[g] |
| Protex ® 14L (metallo) | 6.4% ± 13.6% | 1.75 ± 0.04 | 23.5% ± 4.6% | 5.1% ± 0.7% | 0.00 ± 0.02 | 5.0%-7.5% | n.d.[g] |
| α-Chymotrypsin (serine) | 22.3 ± 17.8% | 0.63 ± 0.01 | 95.8% ± 22.8% | 101.3% ± 2.9% | 0.00 ± 0.01 | 5.0%-7.5% | n.d.[g] |
| Thermolase ® (aspartyl) | 0.0% ± 0.2% | 0.21 ± 0.04 | 89.1% ± 18.5% | 101.8% ± 5.2% | 0.00 ± 0.01 | 2.5%-5.0% | n.d.[g] |

[a]For all tests, minimally required protease concentration to degrade 125 μg ml$^{-1}$ of Fel d 1 under optimal conditions were used (c.f. Table 2) and incubation took place overnight at 37° C.
[b]Keratin hydrolysis by proteases was determined either with keratin azure as surrogate substrate or directly on keratin whereas hydrolysis products were determined by the TNBS assay (data extracted from FIG. 12). Activity on keratin azure was determined as percentage of maximally hydrolysable substrate amount. Activity in the TNBS assay was determined by the absorbance of the formed coupling product at 405 nm. See text for experimental details.
[c]Vitality of keratinocytes in the presence of proteases was determined as described in the text. Two different celltox staining methods were applied (WST-1 and Sulforhodamin B) and vitality was determined as percentage of vitality of keratinocytes that were not incubated with proteases.
[d]Cellulose hydrolysis by proteases was determined with cellulose azure as surrogate substrate. The assay was performed in duplicates and as proposed by the manufacturer (see text for details). The cellulose hydrolysis activity corresponds to the release of the azure dye, which was determined spectrophotomatrically at 575 nm. As positive control served 2.5 units of cellulase from *Aspergillus niger* (Sigma-Aldrich, C1184), which resulted in a absorption of 0.28 ± 0.01.
[e]The inactivation of proteases by isopropanal and Tween 20 ® were determined by estimation of the concentration range at which Fel d 1 degradation by the proteases was reduced by more than 50% (LD$_{50}$). See text for details.
[f]Determined only by a single experiment
[g]n.d., not determined teases papain, bromelain and ficin; the aspartic acid proteases mucorpepsin/rennin, pepsin, aspergillopepsin, endothiapepsin and chymosin; and the zinc-metalloproteases thermolysin (from *Geobacillus*) and endoproteinase Asp-N. Degradation of Fel d 1 to completion could be achieved by increasing the concentration of several other of the proteases. SDS-PAGE further confirmed that these pro- Example 2

In all applications employing protease mediated degradation of Fel d 1, the cat and user would be exposed to protease activity. Filaments of the protein keratin are abundant in keratinocytes in the cornified layer of the epidermis (skin), as well as in hair and nails of both humans and cats.

Therefore, the identification of candidate Fel d 1 proteases with reduced proteolytic activity against keratin would be useful to address safety concerns in the development of products intended for human and animal applications.

Figure 3:
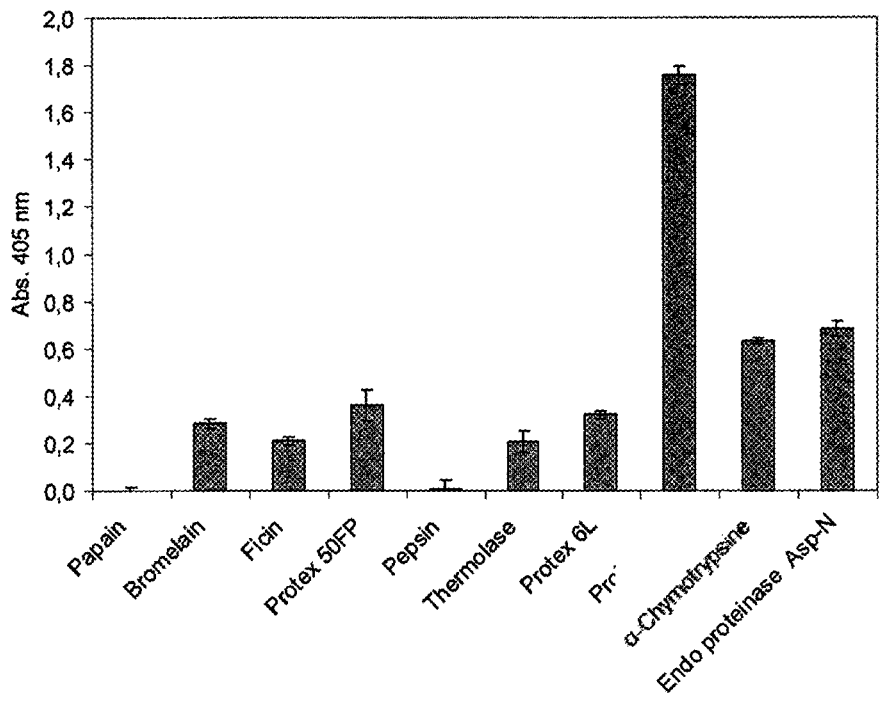
FIG. 3. Histogram showing keratin-hydrolyzing activity of the proteases as determined by TNBS assay. Keratin powder was incubated overnight with the hit proteases at concentrations and under reaction conditions that had been found to be optimal for Fel d 1 degradation (c.f. Table 2). Keratin-degradation products were determined spectrophotometrically at 405 nm in 10-fold dilutions of the samples after coupling reaction with picrylsulfonic acid (TNBS). The data represent the difference between absorbance determined in the samples and in controls with the same buffer but without protease. Average and standard deviation were determined from three independent repetitions of the experiment.
Figure 4:
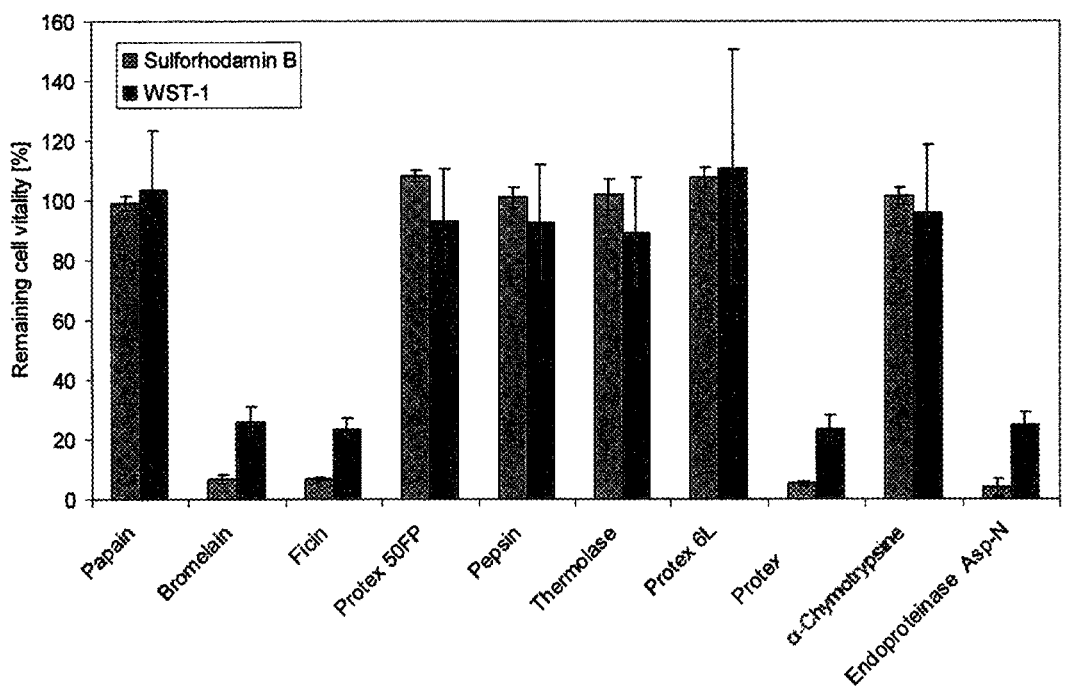
FIG. 4. Histogram showing celltoxic effect of proteases on human keratinocytes as determined by Sulforhodamin B and WST-1 assays. Confluently grown primary human keratinocytes were incubated overnight with hit proteases (in cell cultivation medium) at concentrations that were identified to be minimally required to degrade 125 µg ml$^{-1}$ of Fel d 1 (c.f. Table 2). After incubation, remaining cell vitality was determined for all cells per well (adherent and detached cells) by staining (of metabolically active cells) with WST-1. The remaining cell vitality of the adherent cells alone was then determined by staining (of the proteins of living cells) with Sulfrohodamin B. Cells that were not incubated with proteases served as control (corresponds to 100% remaining cell vitality). Average and standard deviation were determined from three independent repetitions of the experiment.

To characterize the substrate specificity of the active candidate proteases against physiologically relevant proteins, the ability of candidate Fel d 1 hit proteases to hydrolyze keratin was determined. Keratin azure (Sigma-Aldrich, K8500) is composed of azure dye-impregnated sheep's wool keratin and is used as a keratin substrate to quantify protease activity. Keratin azure was incubated overnight with hit proteases under optimal conditions (as determined in the ENZCHEK® protease assay) and at protease concentrations that were found to completely degrade 125 μg $ml^{-1}$ Fel d 1 (Table 2). Degradation of keratin azure was then determined. In three repetitions, a significant degradation activity was only reproducibly determinable with this assay for the thiol proteases bromelain and ficin, which degraded 43.2%±23.3% and 33.1±8.5% of the applied keratin azure, respectively (Table 3). The aspartyl proteases aspergillopepsin from *A. oryzae* (ao aspergillopepsin, PROTEX® 50 FP), endothiapepsin from *Cryphonectria parasitica* (cp endothiapepsin, THERMOLASE®) and pepsin were not active, as they degraded less than 1% of keratin azure in average (Table 3).

To further characterize the keratin degrading activity of hit proteases, an assay was performed that colorimetrically detects keratin degradation products by using a coupling reaction with trinitrobenzene sulfonic acid (TNBS) reagent. This assay enabled the determination of hydrolyzing activity of all tested enzymes using keratin powder from sheep's wool as substrate. Papain and pepsin showed no keratin degrading activity. All other hit proteases were active against keratin substrate. The keratin degrading activity of *Geobacillus* thermolysin was at least two-fold higher compared to all other tested proteases (FIG. 3). The results from the azure keratin assay described above correlated with the results from the TNBS-based keratin assay, with the exception of the two aspartic acid proteases ao aspergillopepsin and cp endothiapepsin (Table 3). For this two aspartic acid proteases and Endoproteinase Asp-N, the buffer conditions may have affected the keratin degrading activity measurements as determined by the TNBS assay. This is because the ammonium acetate buffer (100 mM, pH 4.0) as well as the Endoproteinase Asp-N buffer (which was supplemented by the manufacturer) showed a basal level of keratin degrading activity in the assay in the absence of protease. Moreover, the TNBS-based assay determines proteolysis directly on keratin whereas the keratin azure assay uses a derivatized keratin substrate, which might further explain inconsistencies between the results of the two assays for some of the tested hit proteases.

As a model for living skin cells, the cytotoxic effects of the hit proteases were tested on keratinocytes. A primary cell line of human keratinocytes was cultured to confluence in microplates and tested for cell viability after overnight incubation with the hit proteases at minimal concentrations found to completely degrade 125 μg $ml^{-1}$ Fel d 1 (Table 2). Because cultured mammalian cells are highly susceptible to changes in the composition and pH of cell culture medium, the proteases were directly diluted in the cell culture medium. After overnight incubation with the proteases, water-soluble tetrazolium WST-1 was added to the cell culture (confluent layer and medium) (Cell proliferation reagent WST-1, Roche Diagnostics). The colorless WST-1 is reduced into a yellow dye (formazan) due to electron transfer catalyzed by mitochondrial dehydrogenases of vital cells. Thus, the formation of yellow dye indicates cell vitality of both adherent and detached cells. Cell vitality of adherent cells alone was determined by staining with sulfrohodamin B after overnight incubation with proteases. The red color formation is a measure of protein concentration, which correlates with the adherent cell concentration. Cells that were not incubated with proteases served as a control. For all tested proteases, comparable results were obtained for both assays (FIG. 4, Table 3). As can be seen, a relatively high cytotoxic effect (low remaining cell vitality) was determined for bromelain, ficin, *Geobacillus* thermolysin and endoproteinase Asp-N. All other hit proteases (papain, ao aspergillopepsin, pepsin, cp endothiapepsin, hl subtilisin and alpha-chymotrypsin) had no significant effect on cell vitality as compared to untreated cells (whose cell vitality corresponded to 100%).

For proteases that provoked cytotoxic effects on keratinocytes, skin irritating effects cannot be predicted with certainty because the keratinocytes of the skin are protected by several layers of keratin. However, for proteases that did not provoke cytotoxic effects, skin irritating effects are unlikely.

The results of the cytotoxicity assay (FIG. 4) were less graduated compared to the results of the TNBS keratin degradation assay (FIG. 3). Proteases either had a significant cytotoxic effect or failed to elicit cytotoxicity. Nevertheless, correlations between the results of the two assay were present. For example, papain and pepsin showed no effect in either assay. On the other hand, the cytotoxic effects of bromelain, ficin, *Geobacillus* thermolysin and endoproteinase Asp-N on keratinocytes were confirmed by the TNBS assay.

To further assess papain activity, keratinocytes were incubated in cell culture medium overnight with papain in concentrations 1000-fold greater compared to the minimum required protease concentration shown in Table 2. This resulted in significant cytotoxic effects, with 31% and 8% cell vitality as determined by the WST-1 and sulfurhodamin B assays, respectively. Most cosmetic applications do not require overnight incubation. Microscopy revealed that no significant cell detachment occurred after the first hour of incubation, even in the presence of 1000-fold increased concentration of papain, indicating the absence of cytotoxic effects at this earlier time point.

The effect of the protease preparations on cellulose fibers was tested with cellulose azure (Sigma-Aldrich, St. Louis, Mo.), which is a substrate analogous to keratin azure. This experiment was performed to estimate the effect of the hit protease preparations on cotton textiles. Proteolytic hydrolysis of cellulose was determined using cellulose azure as surrogate substrate. The assay was performed in duplicate and as proposed by the manufacturer. The cellulose hydrolysis activity corresponds to the release of the azure dye, which was determined spectrophotometrically at 575 nm. As a positive control, 2.5 units of cellulase from *Aspergillus niger* (Sigma-Aldrich, C1184) was measured, resulting in an absorption of 0.28±0.01. Of the ten hit proteases, only ao aspergillopepsin (PROTEX® 50 FP) showed significant activity during overnight incubation in the optimal Fel d 1 degradation buffer (Table 2), corresponding to 28%±2% of the activity of the positive control (Table 3). The cellulase activity of this (or any) protease was unexpected because proteases usually do not accept polysaccharides as substrate. Presumably, this protease preparation is a crude extract of protease-overproducing *Aspergillus oryzae* and therefore contains other enzymes that originate from the expression host, such as cellulases.

Most hit proteases showed no or only little keratinolytic activity or cytotoxic effects (FIGS. 3 and 4 and Table 3). Except for ao aspergillopepsin preparation (PROTEX® 50 FP), no hit proteases were active on cellulose azure, indicating their inability to degrade cotton textiles. In addition, the use of high concentrations of proteases such as papain in cosmetic products indicates that their use in applications to degrade Fel d 1 can be safe for both the user and the cat.

Example 3

Potential applications include cleansing agents or wipes, such as for the cleaning of furniture or other surfaces contaminated with Fel d 1. Typical cleansing agents contain solvents, such as denatured ethanol or isopropanol, as disinfectants and to dissolve oil and grease. The isopropanol concentration of a typical bath tub cleaner is 10 to 15%. However, solvents such as isopropanol can inactivate enzymes such as proteases. Therefore, hit proteases were tested for activity in isopropanol-containing media. Because cleaning agents are typically diluted by water, the Fel d 1 degrading activity of the hit proteases was tested in the presence of isopropanol at concentrations between 0 and 12.5%.

Figure 5:
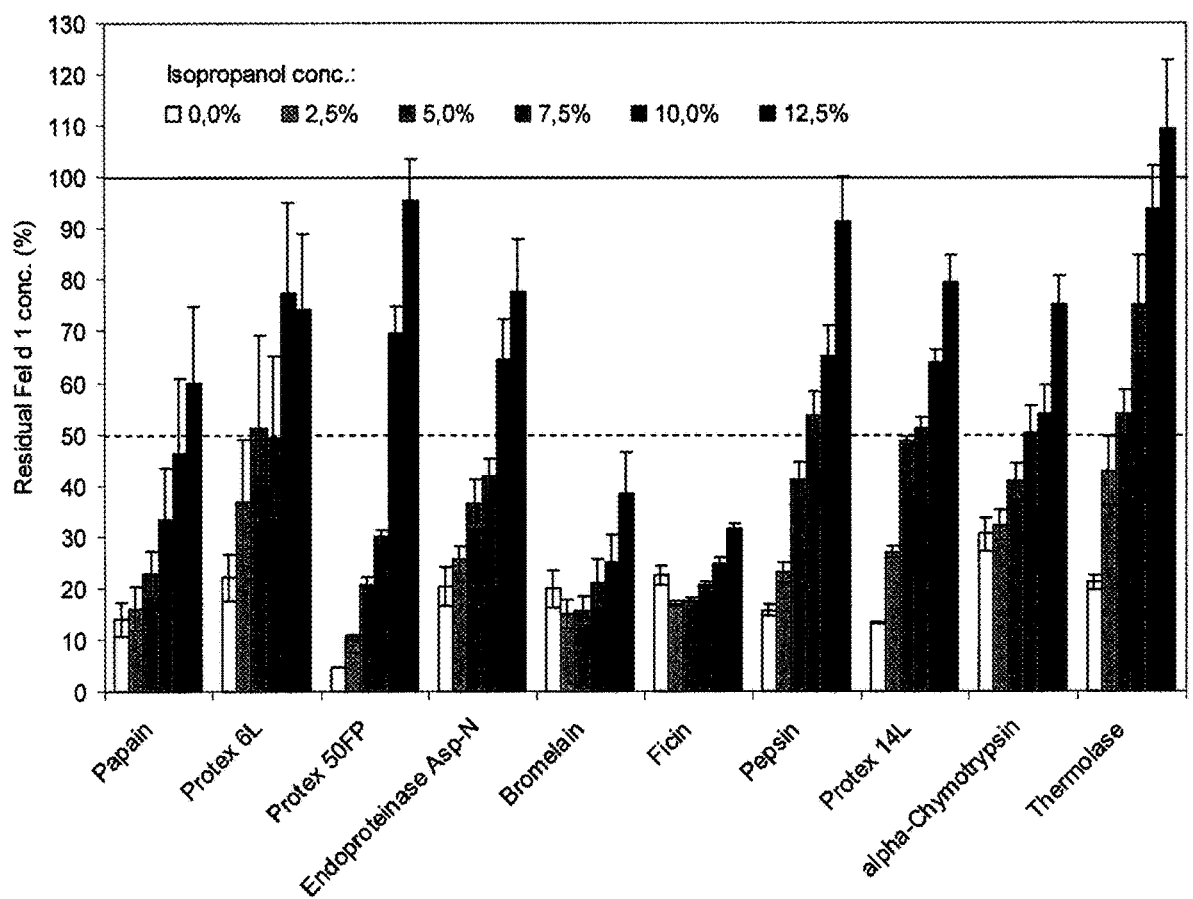
FIG. 5. Histogram showing effect of isopropanol on the protease-catalyzed degradation of Fel d 1. Hit proteases were incubated overnight with 0, 2.5%, 5.0%, 7.5%, 10.0% and 12.5% of isopropanol at concentrations and under reaction conditions that were found to be optimal for Fel d 1 degradation (c.f. Table 2). The samples were diluted and analyzed by ELISA with a time interval of 20 minutes. The indicated residual Fel d 1 concentration represents the percentage of Fel d 1 determined for the samples as compared to the Fel d 1 for the respective buffer controls with maximal isopropanol concentration but without protease. Average and standard deviation were determined from three independent repetitions of the experiment.

Hit proteases were incubated overnight with 0, 2.5%, 5.0%, 7.5%, 10.0% and 12.5% of isopropanol at concentrations and under reaction conditions optimal for Fel d 1 degradation (Table 2). The samples were diluted and analyzed by ELISA with an assay reading time point of 20 minutes. As shown in FIG. 5, the residual Fel d 1 concentration represents the percentage of Fel d 1 determined for the samples as compared to the Fel d 1 for the respective buffer controls with maximal isopropanol concentration but in the absence of protease. FIG. 5 shows averages and standard deviations from three independent repetitions.

With the exception of bromelain and ficin, the activity of all proteases was reduced by at least 50% in the presence of 12.5% isopropanol. The thiol proteases were the least sensitive to isopropanol. Even in the presence of 12.5% of isopropanol, papain, bromelain and ficin degraded about 40% to 70% of the added Fel d 1 (FIG. 5). In an additional experiment with 25% of isopropanol, bromelain and ficin degraded more than 50% of Fel d 1. In contrast, the aspartic acid proteases were the most sensitive to isopropanol. Ao aspergillopepsin (PROTEX® 50 FP), pepsin and cp endothiapepsin were inactivated by more than 90% in the presence of 12.5% isopropanol. As a control. ELISA experiments revealed that isopropanol alone was not found to significantly reduce Fel d 1 concentration. Given this, bromelain or ficin appear to be particularly suitable proteases to degrade Fel d 1 present in dust or on surfaces, using an isopropanol-containing cleaning agent. These proteases actively degraded Fel d 1, even in isopropanol concentrations that exceed those in typical cleaning applications.

Because contact with skin, hair and fur is minimal and transient, the higher keratinolytic activities of bromelain and ficin, compared to the other tested proteases, are not expected to be detrimental. Moreover, bromelain and ficin are generally regarded as safe when used in cosmetics (see above) or in nutrition processing (e.g., as meat tenderizer).

Example 4

Potential applications for reducing Fel d 1 concentration on the fur of the cat include protease-containing shampoos or dry powders, foams/mousses among other compositions. A total of 67 mg of Fel d 1 per cat has been estimated. Although only a small fraction of the allergen becomes airborne, the large amount of Fel d 1 present on the cat indicates the significant benefit afforded by reducing the amount of Fel d 1 in or on the cat's fur and/or skin. The use of conventional pet shampoos on cats has been reported to reduce Fel d 1 concentration in the fur as well as the airborne Fel d 1 concentration in the cat's home. The efficacy of conventional shampoos can be increased by the addition of proteases as described herein.

Most shampoo formulations contain a mix of different surfactants, of which anionic surfactants are the largest class. Non-ionic surfactants are the second largest surfactant class, and have either polyether or polyhydroxyl as a polar group to increase water solubility. Non-ionic surfactants are widely used in topical applications because, they have a reduced ability to cause irritation when compared to anionic surfactants. This property makes non-ionic surfactants attractive for protease-containing pet shampoos. TWEEN® 20 (polysorbate 20) is frequently used as a non-ionic surfactant in nutrients and cosmetics. It is registered as an approved food additive (E-432) in the European Union and also in the INCI index (International Nomenclature of Cosmetic Ingredients). Because it is an approved food additive, TWEEN® 20 can be used as a shampoo ingredient, and would not pose safety issues if the cat accidentally ingests part of it during the washing procedure.

Figure 6:
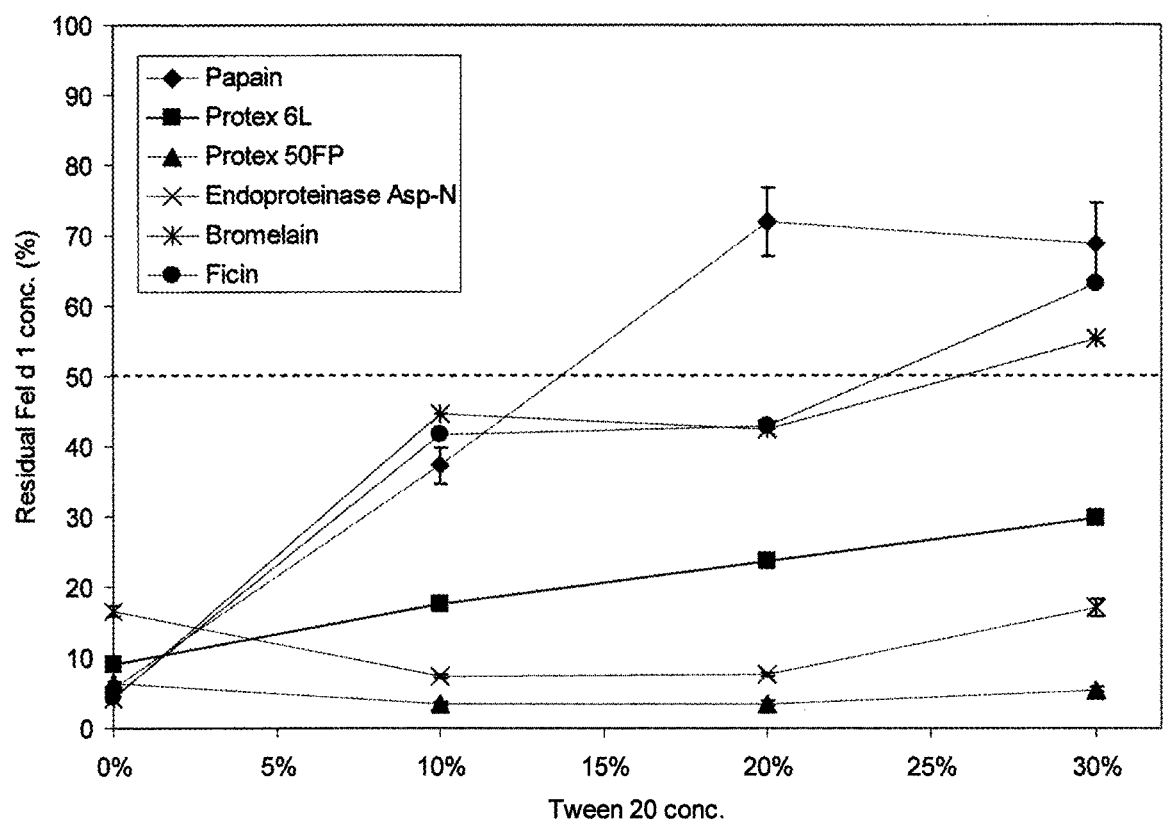
FIG. 6. Graph showing effect of Tween® 20 on the protease-catalyzed degradation of Fel d 1. Hit proteases were incubated overnight with 0, 10%, 20%, and 30% of Tween® 20 at concentrations and under reaction conditions that were found to be optimal for Fel d 1 degradation (c.f. Table 2). The samples were diluted and analyzed by ELISA with a time interval of 20 minutes. The indicated residual Fel d 1 concentration represents the percentage of Fel d 1 determined for the samples as compared to the Fel d 1 for the buffer controls with the respective Tween® 20 concentrations but without protease. Average and standard deviation were determined from three independent repetitions of the experiment.

The effect of TWEEN® 20 on Fel d 1 degrading activity of the hit proteases was tested after overnight incubation with 0, 10%, 20%, and 30% TWEEN® 20 and at protease concentrations and under reaction conditions optimal for Fel d 1 degradation as shown in Table 2. The samples were diluted and analyzed by ELISA with an assay reading time point of 20 minutes. The indicated residual Fel d 1 concentration represents the percentage of Fel d 1 determined for the samples compared to the Fel d 1 for the buffer controls with the respective TWEEN® 20 concentrations but without protease. Averages and standard deviations were determined from three independent repetitions. All tested hit proteases displayed tolerance to TWEEN® 20. Even at the highest tested concentration of 30% TWEEN® 20 none of them was completely inactivated. At 10% TWEEN® 20, more than 50% of the 125 µg ml$^{-1}$ Fel d 1 was degraded for all proteases (FIG. 6, Table 3). Given that a typical shampoo formulation contains about 40% TWEEN® 20 and undergoes approximately 20-fold dilution during application, the proteases would have to be active in concentrations of approximately 2% TWEEN® 20 to retain Fel d 1 degradation activity. Accordingly, all of the hit proteases be predicted as suitable for shampoo applications.

A pH neutral skin product has a pH of approximately 5.5, which corresponds to the pH on the skin. The Fel d 1 degrading activity of the aspartic acid protease ao aspergillopepsin (PROTEX® 50 FP) was not affected by TWEEN® 20 even at the highest tested concentration of 30% (FIG. 6). Although, this protease was found to have the highest activity at pH 4.0 (See Table 2), it still retained 46% activity at pH 6.0 in the ENZCHEK® protease assay. In addition, ao aspergillopepsin (PROTEX® 50 FP), which did not show degradation activity when keratin azure was used as substrate (Table 3), showed only minimal activity against keratin (FIG. 3) and had no significant cytotoxicity toward keratinocytes (FIG. 4). These properties suggest that ao aspergillopepsin (PROTEX® 50 FP) is suitable for use in a protease-containing shampoo for Fel d 1 reduction.

Papain may also be a suitable alternative to ao aspergillopepsin (PROTEX® 50 FP) in shampoo applications. Although papain is less tolerant to TWEEN® 20 than ao aspergillopepsin (PROTEX® 50 FP), it remains active at expected TWEEN® 20 concentrations of 2% during application (FIG. 6). Papain showed comparable Fel d 1 degradation activity at pH 7.4 and pH 6.0, rendering it likely to be suitable for use in a pH neutral shampoo. Papain was not active against keratin in the TNBS assay (FIG. 3) and did not induce significant cytotoxicity against keratinocytes (FIG. 4). Papain was not active on cellulose azure substrate, and is therefore likely not to exhibit degradation activity against cotton textiles (Table 3). Papain is also used at high concentrations in nutrients (meat tenderizer, BBQ sauces) and cosmetics (enzyme peeling) without requiring heat inactivation before use. Papain is likely applicable as a shampoo ingredient, even if the cat accidentally ingests the shampoo during the washing procedure.

Example 5

Another application is a protease-containing product for use in a cat's mouth, including dentifrices, rinses, beverages, foods or treats, strips or films. Such products can reduce Fel d 1 concentration in the mouth of the cat, which is a major source of the allergen. To test the activity of proteases under application-like conditions, a model for cat saliva was established. The preparation of artificial cat saliva was based on published artificial human saliva preparations (McKnight-Hanes & Whitford, 1992, Caries Res. 26: 345-350) (Table 4).

TABLE 4

Composition of artificial cat saliva

| Ingredients | Contents per liter[a] |
|---|---|
| Methyl-p-hydroxybenzoate | 2 g |
| Sodium carboxymethyl cellulose | 10 g |
| KCl | 625 mg |
| $MgCl_2 \times 6H_2O$ | 59 mg |
| $CaCl_2 \times 2H_2O$ | 166 mg |
| $K_2HPO_4$ | 804 mg |
| $KH_2PO_4$ | 326 mg |
| L-Cysteine | 4.85 g |
| Supplements for "extreme conditions"[b] | |
| Fel d 1 | 125 mg |
| Skim milk | 7.14 g |
| Supplements for "normal conditions" | |
| Fel d 1 | 12.5 mg |
| Skim milk | 4.50 g |

[a] The components are solved in water and pH is adjusted to 7.5 with KOH solution
[b] Extreme and normal conditions are benchmarks that refer to allergen and protein concentrations, which are above expected and on average levels, respectively (see text for details)

The pH was adjusted to 7.5, which is the pH of cat saliva. The concentration of Fel d 1 in cat saliva was determined to be between 0.3 to 45 μg/ml (whole cat population) and 2.2 to 12.4 μg/ml for an intermediate group, which is represented by one third of the whole population. The maximum Fel d 1 concentration in the artificial cat saliva was defined as 125 μg ml$^{-1}$, as this concentration was used in all previous experiments, although it exceeded the predicted maximum Fel d 1 concentration in cat saliva by a factor of 2 to 3.

Skim milk, which contains approximately 35% protein, was used to simulate the protein content in the saliva. Skim milk also contains other components such as carbohydrates, which are related to the complex composition of real saliva and are therefore predicted to render the model more realistic. Human saliva from different individuals has been reported to contain between 0.67 and 2.37 mg ml$^{-1}$ of protein (as determined by different techniques with bovine serum albumin as standard). This estimate was used as an approximation for the protein content in cat saliva. A maximum protein content of 2.5 mg ml$^{-1}$ was defined for the artificial cat saliva, which was represented by 7.14 mg ml$^{-1}$ skim milk. As discussed above, cysteine has been found to activate certain proteases for Fel d 1 degradation. The effect was most prominent for thiol proteases, such as papain, bromelain and ficin (see above).

Figure 7:
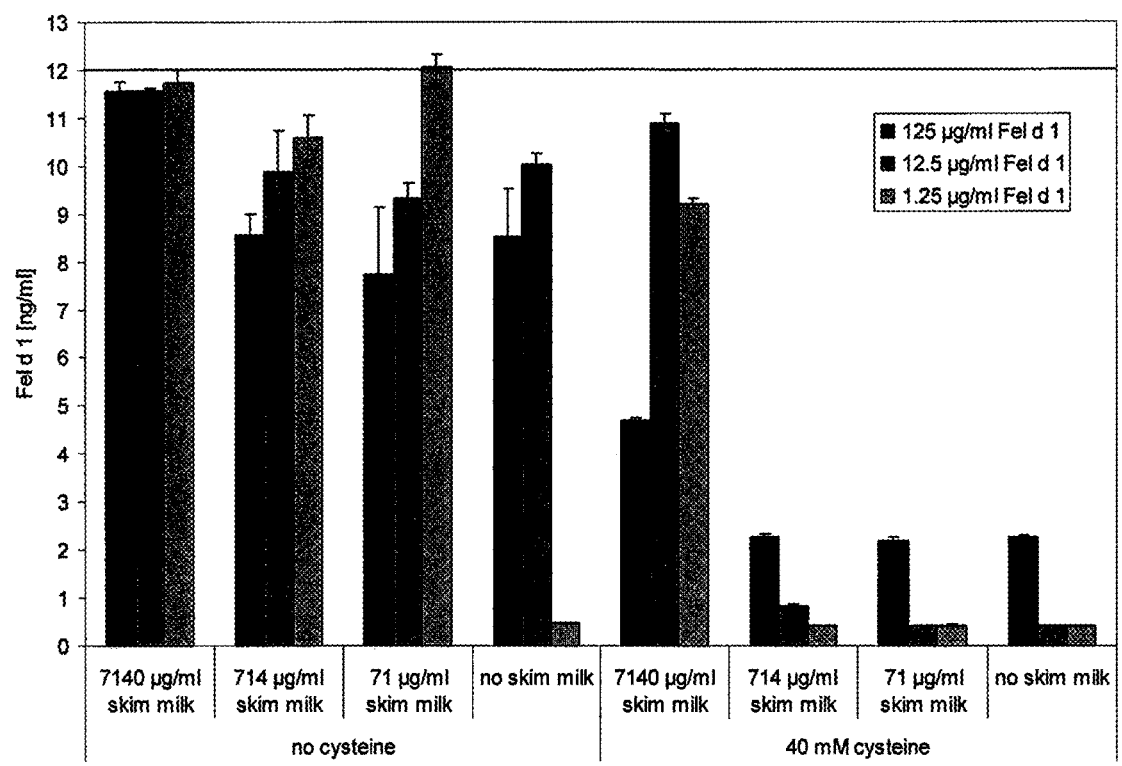
FIG. 7. Histogram showing effect of cysteine and different concentrations of skim milk on the papain-catalyzed degradation of different concentrations of Fel d 1 in artificial cat saliva during overnight incubation at 37° C. 1.25, 12.5 and 125 µg ml$^{-1}$ natural Fel d 1 was incubated overnight with 4.65 µg ml$^{-1}$ of papain (corresponds to 60 rfu s$^{-1}$ in 20 µl reaction mix, c.f. Table 2) at 37° C. in artificial cat saliva with 0, 71, 714 and 7140 µg ml$^{-1}$ skim milk with and without 40 mM of cysteine. After incubation, the samples were diluted and analyzed by ELISA with a time interval of 30 minutes. As a result of the dilution, a maximal concentration of 12 ng ml$^{-1}$ of Fel d 1 was expected (i.e., in the absence of degradation). Average and standard deviation were determined from two independent repetitions of the experiment.

The effects of different concentrations of Fel d 1 and skim milk, as well as the requirement of cysteine for Fel d 1 degradation in artificial saliva, were tested using the hit protease papain with overnight incubation at 37° C. (FIG. 7). Papain was used at the minimum concentration required to completely degrade 125 μg ml$^{-1}$ Fel d 1 under optimal conditions, i.e. in sodium phosphate buffer at pH 7.8 (Table 2). Similar to the previous experiments conducted in buffer, 40 mM of L-cysteine was shown to be essential for efficient degradation of Fel d 1 by papain in artificial cat saliva (FIG. 6); however, this requirement could be satisfied by other components of the formulation, especially in an edible compositions such as a food, beverage or treat.

Although, reaction conditions in artificial cat saliva differed significantly from the optimal reaction conditions reported in Table 2, most of the added 125 μg ml$^{-1}$ Fel d 1 was degraded during overnight incubation (in the presence of cysteine) for skim milk concentrations up to 714 μg ml$^{-1}$ (FIG. 7). Nevertheless, Fel d 1 degradation activity decreased with increasing skim milk concentration, probably due to the increased protein concentration. Skim milk proteins predominantly consist of casein, and casein was shown to be hydrolyzed by papain via the ENZCHEK® protease assay, which uses labeled casein as substrate (Table 2). Casein and Fel d 1 thus represent competing substrates for the degradation by papain. Therefore, the concentration of papain would need to be increased to completely degrade Fel d 1 at the highest skim milk concentration (and in the presence of cysteine). Moreover, an increased papain concentration would likely result in a faster Fel d 1 degradation, which would be preferred in order to degrade Fel d 1 in the saliva within the time frame in which the cat consumes the protease-containing pet food or beverage, or is otherwise orally exposed to a protease-containing formulation.

Two types of artificial cat saliva were developed for further testing (Table 4). The first type represented "extreme conditions," and contained 125 μg ml$^{-1}$ of Fel d 1 (2 to 3-fold higher concentration than the maximum concentration determined in cat saliva) and 7140 μg ml$^{-1}$ of skim milk (corresponding to the maximally determined protein content in human saliva). These allergen and protein concentrations are above expected levels and are provided to estimate the surplus activity of proteases in a pet food application. The second type represented "normal conditions," and contained 12.5 μg ml$^{-1}$ of Fel d 1 (representing the upper border of Fel d 1 concentrations as determined in the intermediate cat group) and 4.5 μg ml$^{-1}$ of skim milk (corresponding to the average protein concentration in human saliva of 1.6 μg ml$^{-1}$). These allergen and protein concentrations represent an average level expected in the saliva of most cats.

To identify the protease activity required to degrade Fel d 1 in artificial cat saliva (under normal and extreme conditions) within a relatively short period of time, the hit proteases papain, bl subtilisin (PROTEX® 6 L), ao aspergillopepsin (PROTEX® 50 FP) and endoproteinase Asp-N were evaluated by additional kinetic analysis at higher enzyme activities. Preliminary experiments revealed that up to a 1000-fold increase of papain, from 4.5 μg ml$^{-1}$ (corresponding to the minimum concentration required to completely degrade Fel d 1 under optimal conditions during an overnight incubation, Table 2) to 4500 µg ml$^{-1}$, is required to completely degrade Fel d 1 in artificial cat saliva under extreme conditions within 1 hour of incubation.

Figure 8:
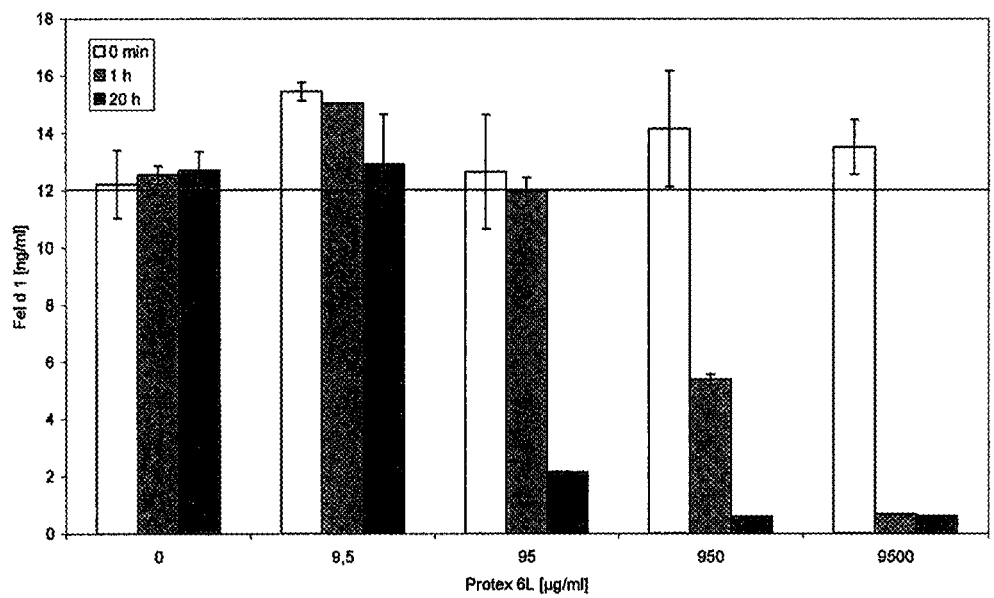
FIG. 8. Histogram showing determination of Fel d 1 by ELISA after incubation for 1 hour and overnight at 37° C. with different concentrations of Bacillus licheniformis subtilisin (Protex® 6 L) in artificial cat saliva (extreme conditions). 125 µg ml$^{-1}$ natural Fel d 1 was incubated for 0 min, 1 hour or 20 hours (overnight) with 0, 9.5, 95, 950 and 9500 µg ml$^{-1}$ of the subtilisin at 37° C. in artificial cat saliva (extreme conditions). Reaction was stopped by addition of 1 mM PMSF. Samples were diluted and analyzed by ELISA with a time interval of 30 minutes. As a result of the dilution, a maximal concentration of 12 ng ml$^{-1}$ of Fel d 1 was expected (i.e., in the absence of degradation). Average and standard deviation were determined from two independent repetitions of the experiment.

Therefore, for bl subtilisin, amounts that were 10-fold, 100-fold, and 1000-fold greater than 9.5 µg ml$^{-1}$ bl subtilisin, which was the minimum concentration of protease required to degrade 125 µg ml$^{-1}$ Fel d 1 under optimal conditions during an overnight incubation (Table 2) were tested in artificial cat saliva under extreme conditions for Fel d 1 degradation after one and 20 hours of incubation at 37° C. (FIG. 8). Thus, 125 µg ml$^{-1}$ natural Fel d 1 was incubated for 0 min, 1 hour or 20 hours (overnight) with 0, 9.5, 95, 950 and 9500 ml$^{-1}$ of bl subtilisin at 37° C. in artificial cat saliva (extreme conditions, c.f. Table 4). The reaction was stopped by the addition of 1 mM PMSF. Samples were diluted and analyzed by ELISA with an assay reading time point of 30 minutes. Taking into account the dilution, a maximum concentration of 12 ng ml$^{-1}$ of Fel d 1 was expected (i.e. without accounting for the possibility of degradation). Averages and standard deviations were determined from two independent repetitions of the experiment. Similar to the preliminary experiments with papain, a 1000-fold higher bl subtilisin concentration was required to completely degrade Fel d 1 within 1 hour in artificial cat saliva under extreme conditions (FIG. 8).

Figure 9:
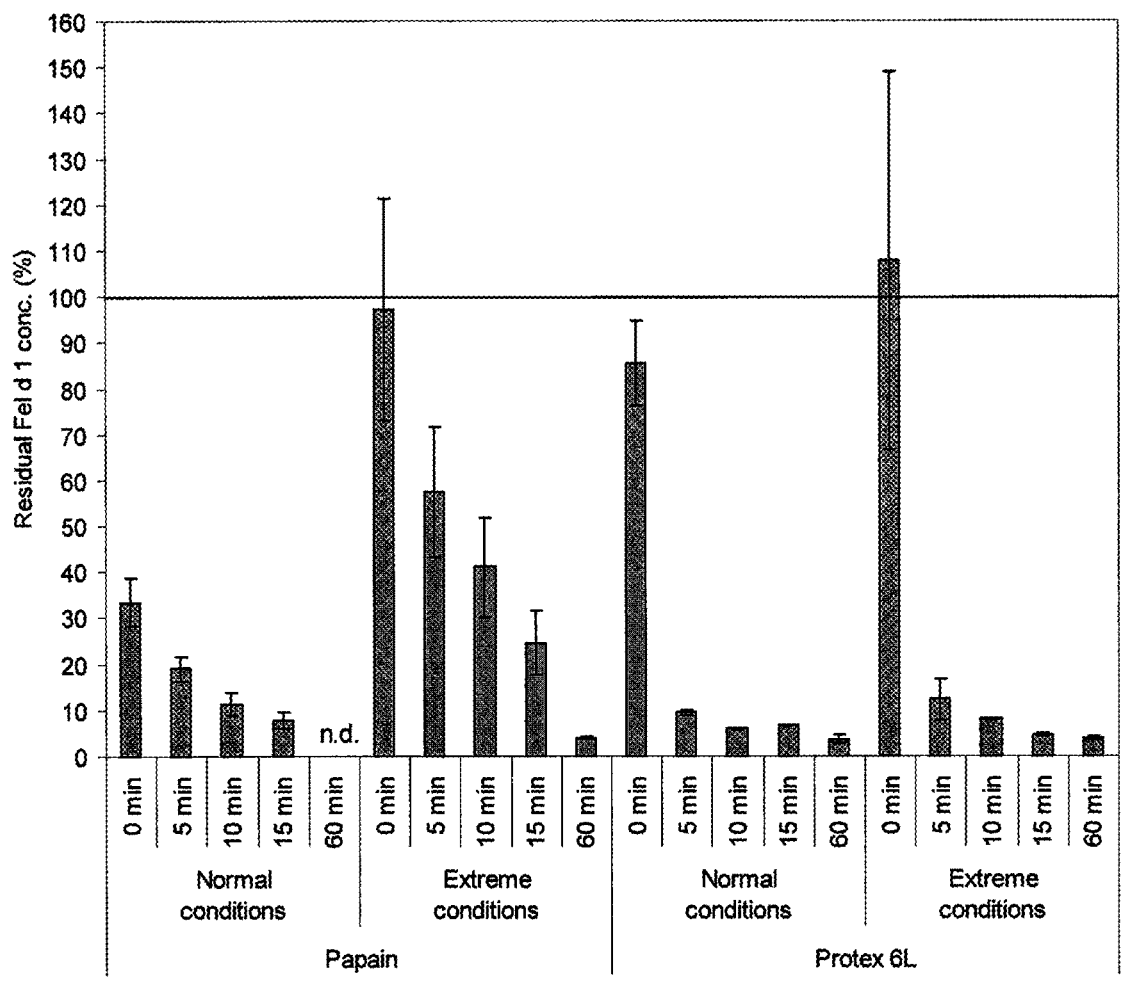
FIG. 9. Histogram showing results of testing papain and Bacillus licheniformis subtilisin (Protex® 6 L) at 1000-fold increased concentrations for the degradation of Fel d 1 in artificial cat saliva after incubation for 5 to 60 min. 4.5 mg ml$^{-1}$ of papain and 9.5 mg ml$^{-1}$ of the subtilisin were incubated for 0, 5, 10, 15 and 60 min with Fel d 1 in artificial cat saliva at 37° C. under normal and extreme conditions. Reaction was stopped by addition of 100 µM E64 (for papain) and 1 mM PMSF (for subtilisin). Samples were diluted and analyzed by ELISA with a time interval of 30 minutes. The indicated residual Fel d 1 concentration represents the percentage of Fel d 1 determined for the samples as compared to the Fel d 1 for the respective buffer controls without protease. Average and standard deviation were determined from three independent repetitions of the experiment. Abbr.: n.d., not determined FIG. 10. Histogram showing results of testing different combinations of papain and Bacillus licheniformis subtilisin (Protex® 6 L) concentrations (at constant ratio) for the degradation of Fel d 1 in artificial cat saliva after incubation for 0 to 60 min. The different combinations of papain and subtilisin concentrations (4.5 and 9.5 µg ml$^{-1}$; 45 and 95 µg ml$^{-1}$; 450 and 950 µg ml$^{-1}$; 4500 and 9500 µg ml$^{-1}$ of papain and subtilisin, respectively) were incubated for 0, 5, 10, 15 and 60 min with Fel d 1 in artificial cat saliva at 37° C. under normal and extreme conditions. Reaction was stopped by addition of 100 µM E64 and 1 mM PMSF. Samples were diluted and analyzed by ELISA with a time interval of 30 minutes. The indicated residual Fel d 1 concentration represents the percentage of Fel d 1 determined for the samples as compared to the Fel d 1 for the respective buffer controls without protease. Average and standard deviation were determined from two independent repetitions of the experiment.
Figure 10:
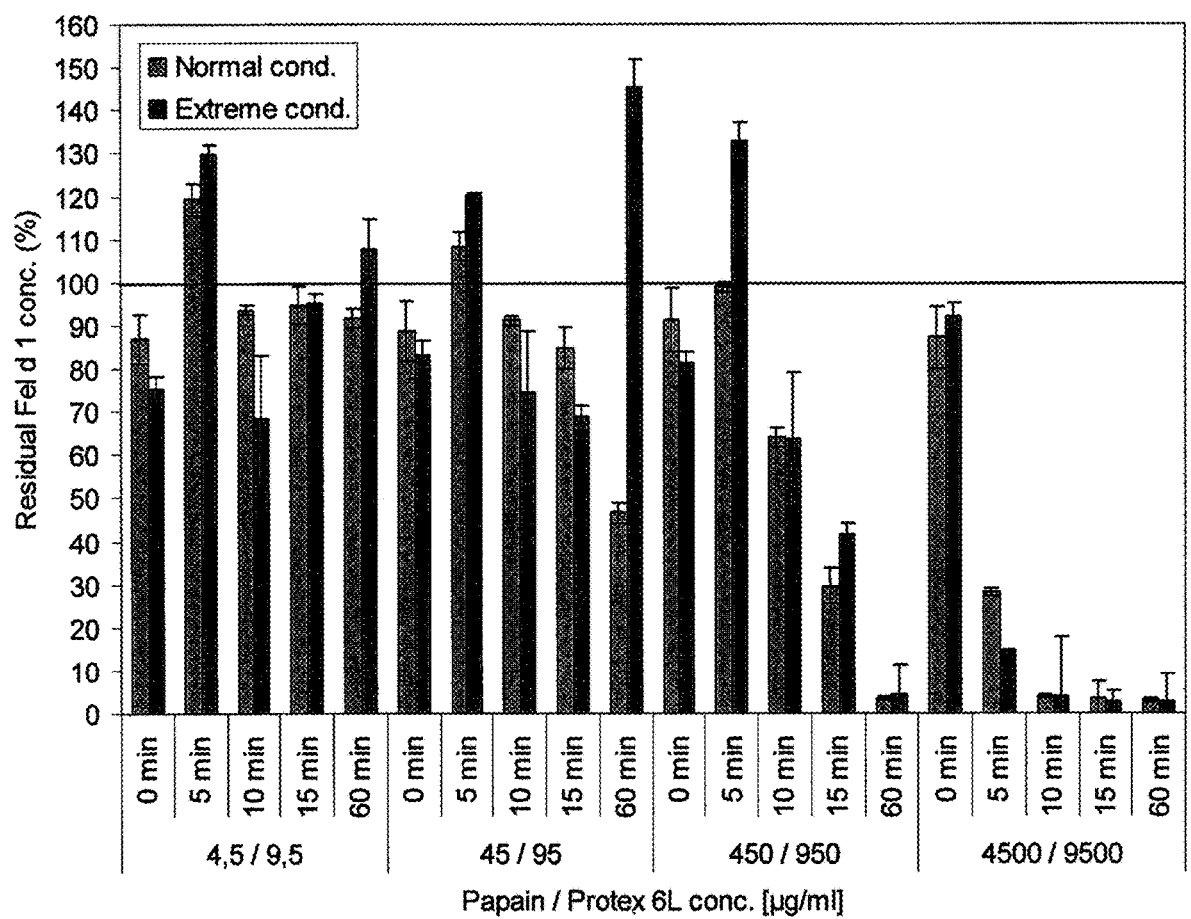
Figure 11:
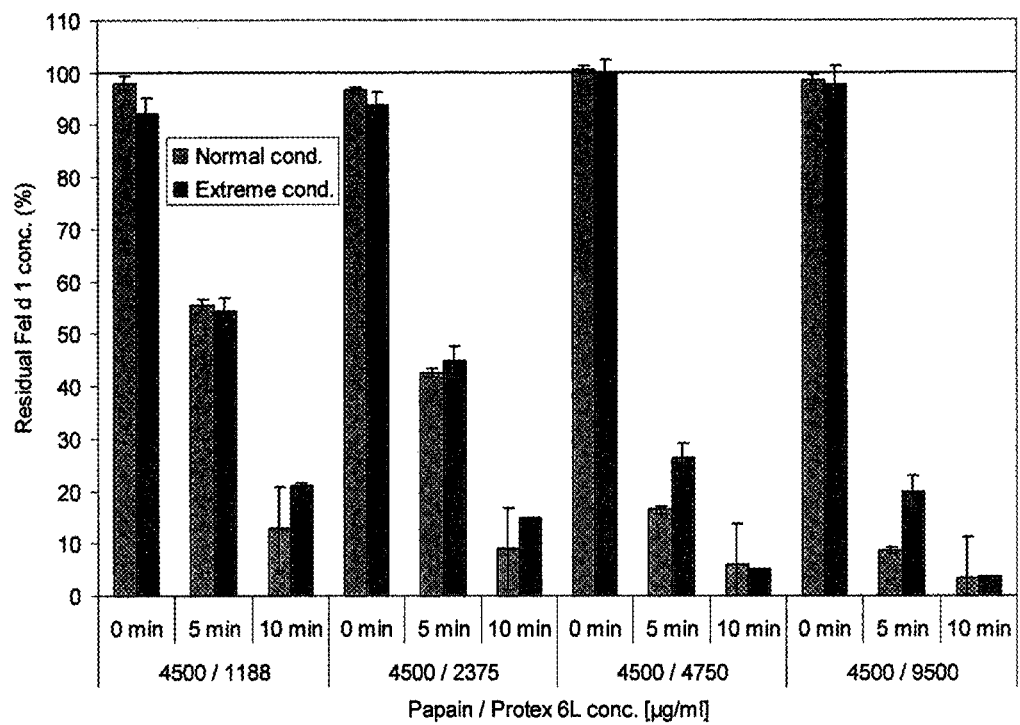
FIG. 11. Histogram showing results of testing different combinations of papain and Bacillus licheniformis subtilisin (Protex® 6 L) concentrations (with constant papain concentration) for the degradation of Fel d 1 in artificial cat saliva after incubation for 0 to 10 min. The different combinations of papain and subtilisin concentrations (4500 and 1188 µg ml$^{-1}$; 4500 and 2375 µg ml-1; 4500 and 4750 µg ml-1; 4500 and 9500 µg ml-1 of papain and subtilisin, respectively) were incubated for 0, 5 and 10 min with Fel d 1 in artificial cat saliva at 37° C. under normal and extreme conditions. Reaction was stopped by addition of 100 µM E64 and 1 mM PMSF. Samples were diluted and analyzed by ELISA with a time interval of 30 minutes. The indicated residual Fel d 1 concentration represents the percentage of Fel d 1 determined for the samples as compared to the Fel d 1 for the respective buffer controls without protease. Average and standard deviation were determined from two independent repetitions of the experiment.
Figure 12:
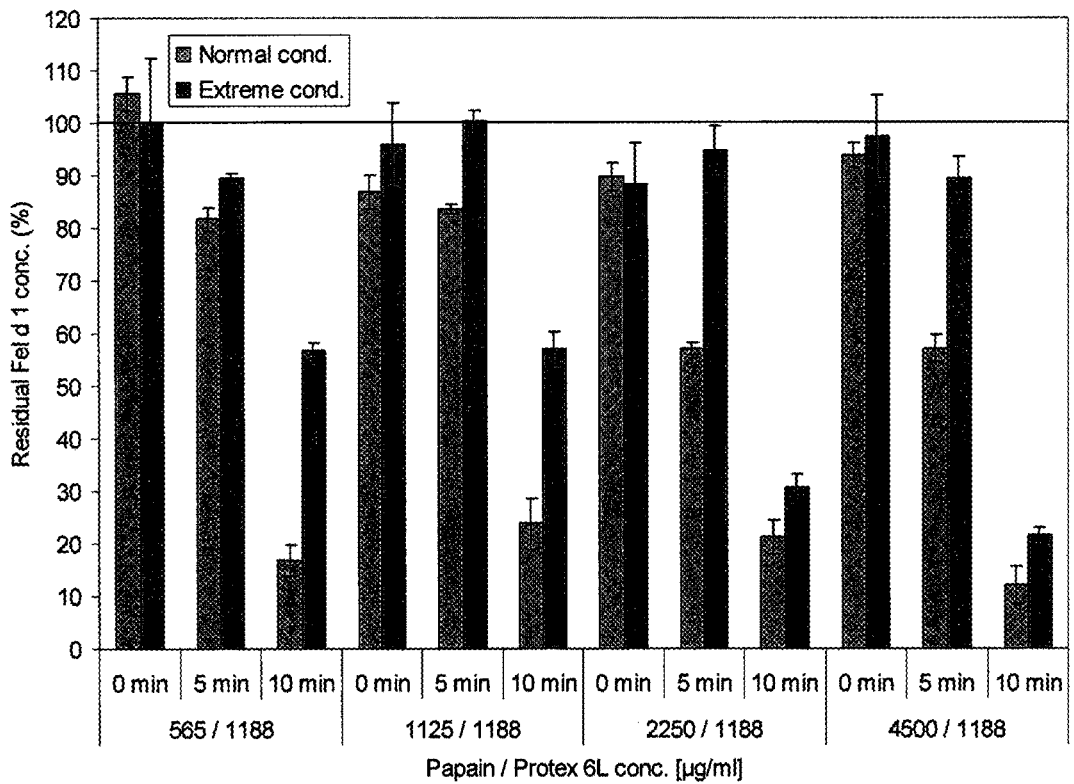
FIG. 12. Histogram showing results of testing different combinations of papain and Bacillus licheniformis subtilisin (Protex® 6 L) concentrations (with constant subtilisin concentration) for the degradation of Fel d 1 in artificial cat saliva after incubation for 0 to 10 min. The different combinations of papain and subtilisin concentrations (565 and 1188 µg ml$^{-1}$; 1125 and 1188 µg ml$^{-1}$; 2250 and 1188 µg ml$^{-1}$; 4500 and 1188 µg ml$^{-1}$ of papain and subtilisin, respectively) were incubated for 0, 5 and 10 min with Fel d 1 in artificial cat saliva at 37° C. under normal and extreme conditions. Reaction was stopped by addition of 100 µM E64 and 1 mM PMSF. Samples were diluted and analyzed by ELISA with a time interval of 30 minutes. The indicated residual Fel d 1 concentration represents the percentage of Fel d 1 determined for the samples as compared to the Fel d 1 for the respective buffer controls without protease. Average and standard deviation were determined from two independent repetitions of the experiment.

To further determine the efficacy of the proteases in 1000-fold excess, Fel d 1 degradation by papain and bl subtilisin was kinetically analyzed in artificial cat saliva under normal and extreme conditions at shorter incubation times (FIG. 9). Papain and 9.5 mg ml$^{-1}$ of bl subtilisin were incubated for 0, 5, 10, 15 and 60 min with Fel d 1 in artificial cat saliva at 37° C. under normal and extreme conditions (Table 4). Reactions were stopped by addition of 100 µM E64 (for papain) and 1 mM PMSF (for bl subtilisin). Samples were diluted and analyzed by ELISA with an assay reading time point of 30 minutes. The residual Fel d 1 concentration represents the percentage of Fel d 1 determined for the samples as compared to the Fel d 1 for the respective buffer controls without protease. Averages and standard deviations were determined from three independent repetitions. Most of the Fel d 1 was degraded already after 5 min with 121 subtilisin (9.5 mg ml$^{-1}$) in artificial cat saliva under both normal and extreme conditions. The experiments revealed that bl subtilisin was somewhat more effective than papain. However, under normal conditions, which correspond to the average composition of cat saliva, more than 80% of Fel d 1 was degraded by papain (4.5 mg ml$^{-1}$) within 5 minutes (FIG. 9). The apparent Fel d 1 degradation activity under these conditions at 0 min could potentially be explained by residual activity despite immediate addition of E64 inhibitor to terminate the reaction. This effect was avoided in the following experiments by the addition of both inhibitors, E64 and PMSF, to terminate activity of papain and bl subtilisin combinations (FIGS. 10-12).

In the context of a pet food application, where a cat with average Fel d 1 and protein concentration in the saliva takes about five to ten minutes to eat food, both papain and bl subtilisin, present in the concentrations tested, would be predicted to degrade the allergen by more than 80% within 5 minutes. Both concentrations tested, 4.5 mg ml$^{-1}$ papain and 9.5 mg ml$^{-1}$ bl subtilisin, respectively, are present at concentrations that are in massive excess over the applied Fel d 1 (125 µg ml$^{-1}$). However, this excess enzyme promotes the accelerated degradation of Fel d 1, such that most of it is degraded within a few minutes.

Different combinations of papain and bl subtilisin were tested to identify synergistic effects on Fel d 1 degradation, which would permit a decrease in the total concentration of proteases, while maintaining efficacy of allergen degradation comparable to that of a single protease in the final cat food application. The thiol protease papain and the bl subtilisin belong to different mechanistic families of proteases and therefore have different substrate specificities. While not intending to be limited to a particular mechanism, it is thought that the two proteases could act synergistically by mutually uncovering new cleavage sites on the Fel d 1 polypeptide chain, resulting in a faster and more effective degradation compared to the degradation achieved by using only a single protease.

The two proteases were tested in combination for their ability to synergistically degrade Fel d 1 in artificial cat saliva at the concentrations previously tested for each protease alone (4500 µg ml$^{-1}$ of papain and 9500 µg ml$^{-1}$ of bl subtilisin, FIG. 9). In addition, Fel d 1 degradation was tested at protease concentrations reduced by a factor of 10, 100 and 1000. 450 µg ml$^{-1}$ papain and 950 µg ml$^{-1}$ bl subtilisin were minimally required to completely degrade Fel d 1 within one hour (FIG. 10). At the combination with highest tested protease concentrations (4500 µg ml$^{-1}$ papain and 9500 µg ml$^{-1}$ bl subtilisin) complete Fel d 1 degradation was achieved after 10 minutes (FIG. 10). This effect was comparable to the effect of 9500 µg ml$^{-1}$ hl subtilisin alone (FIG. 9).

To evaluate the contribution of bl subtilisin, its concentration was varied from 1188 to 9500 µg ml$^{-1}$ while keeping the concentration of papain constant (at 4500 µg ml$^{-1}$) (FIG. 11). Only a small difference in Fel d 1 degradation was observed when 4500 µg ml$^{-1}$ papain was combined with 9500 or 4750 µg ml$^{-1}$ bl subtilisin. Therefore, a combination of 4500 µg ml$^{-1}$ papain and 4750 µg ml$^{-1}$ hl subtilisin would be sufficient to degrade most Fel d 1 present in cat saliva within 10 minutes, even under extreme conditions. Under normal conditions, which is the case for most cats, the combination with the lowest bl subtilisin concentration (1188 µg ml$^{-1}$) is sufficient to degrade about 90% of Fel d 1 within 10 minutes.

To evaluate the contribution of papain, its concentration was varied from 565 to 4500 µg ml$^{-1}$ while keeping the concentration of bl subtilisin constant at the lowest previously tested concentration (1188 µg ml$^{-1}$) (FIG. 12). Under extreme conditions, a reduction of 80% of Fel d 1 in 10 minutes was only achieved when combined with 4500 µg ml$^{-1}$ papain (FIG. 12). In contrast, under normal conditions, the tested papain concentration did not significantly influence Fel d 1 degradation after 10 minutes of incubation. Therefore, the minimum protease combination of 565 µg ml$^{-1}$ papain and 1188 µg ml$^{-1}$ bl subtilisin would be sufficient to reduce Fel d 1 content in the saliva of an average cat by approximately 80% within 10 minutes of incubation, e.g. while the cat is eating the pet food or treat, or drinking a beverage containing the proteases, or otherwise being orally exposed to the protease-containing formulation.

Example 6

A wipe prototype containing functional proteases was developed and tested for inactivation of Fel d 1. A batch of cotton wipes (20 cm×20 cm) containing active PROTEX® 6 L was manufactured and tested for Fel d 1 inactivation. The wipe was successful in degradation of Fel d 1. The specifics are discussed in detail below.

First, the concentration of PROTEX® 6 L required for the wipe was determined. The required enzyme concentration is dependent on the amount of Fel d 1 that has to be inactivated by the prototype. Based on the data provided by Nestlé Purina, the amount of Fel d 1 in the environment that should be digested by the wipe prototype is approx. 25 ng/cm2 (=0.25 mg/m2).

For a wipe prototype, it is not possible to simply set the desired enzyme concentration since the binding capacity for the enzyme might be limited by the available binding/cross-linking sites of the solid material. Therefore the aim was to maximize the amount of immobilized PROTEX® 6 L.

Table 5 summarizes the application- and safety-relevant properties of the hit proteases analyzed herein based on the data from Table 3. It was discovered that protease PROTEX® 6 L combines all characteristics required for development of application prototypes, including those of Examples 6-10: It shows only weak effects on keratin hydrolysis, no effects on viability of keratinocytes, no cellulose activity but high tolerability towards non-ionic detergents. Therefore, PROTEX® 6 L was used for the development of the present prototypes (wipes, cat litter, shampoo, cleansing liquid).

TABLE 5

Summary of properties of hit proteases

| Enzyme | Keratin Hydrolysis | Cytotoxicity In keratinocytes | Detergent Tolerability | Cellulose hydrolysis |
|---|---|---|---|---|
| Papain | No | No | Low | No |
| Protex ® 6L | Low | No | High | No |
| Protex ® 50FP | Low | No | High | Medium |
| Endoproteinase Asp-N | Medium | Strong | High | No |
| Bromelain | Low | Strong | Medium | No |
| Ficin | Low | Strong | Medium | No |
| Pepsin | No | No | n.d. | No |
| Protex ® 14L | Strong | Strong | n.d. | No |
| Alpha-chymotrypsin | Medium | No | n.d. | No |
| Thermolase ® | Low | No | n.d. | No | n.d.: not determined

Immobilization of PROTEX® 6 L on Cotton Wipes
    Fabrication of Cotton Wipes

From the numerous types of cotton fabrics, molton was chosen for the fabrication of the wipes. Molton fabric consists of 100% cotton fibers. Its roughened surface and its high water absorption make it to a versatile cleaning tissue. The size of one final wipe is approx. 20 cm×20 cm.

Cross-Linking Systems for Immobilizing PROTEX® 6 L

In theory, immobilization of enzymes on solid material can be achieved by covalent coupling of the enzyme via a chemical reaction. However, there are no well-established protocols available that describe the coupling of PROTEX® 6 L to cotton fibers.

A first screening of conditions for the immobilization of PROTEX® 6 L used not only the enzyme and carrier (cotton wipe) but also two cross-linkers since the carrier material (cotton) does not possess groups that readily form covalent bonds. The cross-linker used is a 2-component system: a diamine (pentaethylenehexamine, PEHA) and a dialdehyde (glutaraldehyde, GA). They are combined in a fixed ratio and reference is mostly made to the glutaraldehyde concentration to indicate the amount used in proportion to the enzyme.

The 2-component cross-linking system has to match the amount of protein. It was found that the amount used in proportion to PROTEX® 6 L is critical as too low amounts will not cross-link all the enzyme or will results in unstable formulations. Too high amounts will give overcross-linking reducing conformational freedom and subsequently reducing the activity of the enzyme.

Enzymatic Assay for Determining Immobilization Efficiency

In order to monitor the success of the different cross-linking conditions and protocols, the enzymatic activity after cross-linking and washing was determined. At that stage, it is inconvenient and time consuming to directly determine the Fel d 1 degrading activity of cross-linked PROTEX® 6 L by ELISA. To allow a much faster screening of cross-linking conditions, two other enzymatic assays were chosen: The NPA assay, which is based on hydrolysis of the substrate p-nitrophenylacetate by the protease or the ELU test, which is based on the hydrolysis of ethyl lactate. After establishing the final protocol for cross-linking PROTEX® 6 L on small cotton wipes, large scale immobilizations on entire wipes will be performed. Then the capability of degrading Fel d 1 and the enzymatic stability will be directly tested on the target substrate Fel d 1 by ELISA.

Final Production of Immobilized PROTEX® 6 L on Cotton Wipes

Cross-linker amounts and conditions as well as enzyme loadings amounts and conditions were experimentally determined. After which, big-scale reactions were performed to cross-link PROTEX® 6 L on complete wipes (20 cm×20 cm). In detail, liquid PROTEX® 6 L (9.24 ml of 4600 ELU/ml PROTEX® 6 L) was mixed with 83.2 ml phosphate buffer (100 mM, pH 6.5) and glutaraldehyde was added (133 mM final concentration). Cross-linking of the enzyme occurred by incubating the wipe in the reaction mixture over-night at room-temperature. The wipe was washed with water and the liquid is squeezed out and washed again with water and 3% PEG. Finally, the wipe is dried with a stream of air (21° C.) for 5 h.

In summary, PROTEX® 6 L was immobilized on 10 cotton wipes, another 10 control wipes were produced the same way, with the exception that no enzyme was added to the reaction mixture. The wipes were then tested for application. The capability of Fel d 1 inactivation was determined.

Example 7

Cat litter prototypes containing functional proteases were developed and tested for inactivation of Fel d 1. Specifically, 260 g cat litter (perlite) containing active PROTEX® 6 L was manufactured and tested for Fel d 1 inactivation. The cat litter was successful in degradation of Fel d 1. The specifics are discussed in detail below.

First, the concentration of PROTEX® 6 L required for the prototype was determined. The required enzyme concentration is dependent on the amount of Fel d 1 that has to be inactivated by the prototype. Based on the data provided by Nestlé Purina, the amount of Fel d 1 that should be inactivated by the cat litter is approx. 250 mg.

In case of cat litter, it is not possible to simply set the desired enzyme concentration since the binding capacity for the enzyme might be limited by the available binding/cross-linking sites of the solid material. Therefore the aim was to maximize the amount of immobilized PROTEX® 6 L.

Immobilization of PROTEX® 6 L on Cat Litter

Immobilization on Bentonite

"Purina Tidy Cats non clumping cat litter Instant Action" was tested for the immobilization of PROTEX® 6 L. The cat litter is based on the clay mineral bentonite. PROTEX® 6 L was diluted with water and added to bentonite to check possible immobilization conditions and absorption of the enzyme. However, adding water to PROTEX® 6 L dilutes down the 50% glycerol present in this enzyme mixture and makes the bentonite fall apart.

Another immobilization test on bentonite was performed with minimal use of liquid. To this purpose small amounts of PROTEX® 6 L that could be readily absorbed were added directly to the bentonite. Besides the enzyme and carrier two cross-linkers were added since the carrier materials do not possess groups that readily form covalent bonds. The cross-linker used is a 2-component system: a diamine (pentaethylenehexamine, PEHA) and a dialdehyde (glutaraldehyde, GA), which are combined in a fixed ratio. It turned out that a maximum loading is 150-200 µl of liquid per gram of bentonite. The liquid has to be administered individually to each particle. Due to the fact that the particles fall apart, no work-up is possible after immobilization. This is not an immediate drawback but dust with enzyme will get airborne after the bentonite has been wet and dried up again. However, PROTEX® 6 L on this carrier lost all activity after a couple of days, even when dry. In conclusion, the tested cat litter was not suited for the immobilization of PROTEX® 6 L.

Immobilization on Sand

Sand with a particle size of 1.2 mm was tested as another carrier which could be principally be mixed with bentonite. Again two cross-linkers were used besides the enzyme. Sand was used to demonstrate the viability of the approach where the enzyme is immobilized on a second carrier (sand), which could then be mixed with other cat litter particles. A maximum loading of 200 µl PROTEX® 6 L was used per gram of sand. However, the activity and recovery was relatively low, most likely because sand lacks pores and has a small surface area. Leaching of the enzyme is low and thus sand is in principle a suitable material for covalent linkage.

Immobilization on Perlite

Perlite was chosen as a third carrier. Due to its particle size of 2.8-6 mm, it could also principally be mixed with bentonite. Again two cross-linkers (GA and PEHA) were used besides the enzyme to induce covalent bonding. First immobilization experiments showed that the recovery as well as the leaching of the enzyme PROTEX® 6 L is relatively good for enzyme loadings in the lower range. Enzyme loadings above 500 µl/g give significant coloration of the perlite particles but with loadings in the lower range it maintains a bright white color.

Final Production of Immobilized PROTEX® 6 L on Perlite

Clearly, for cross-linking of PROTEX® 6 L to cat litter material, perlite turned out to be superior to sand and bentonite. Perlite permits high enzyme loading, while keeping enzyme leaching low. Moreover, its particle size allows homogenous mixing with other cat litter material. Therefore, perlite was found to be an excellent material for cross-linking of PROTEX® 6 L and finally 260 g perlite containing PROTEX® 6 L were produced.

In detail, liquid PROTEX® 6 L (60 ml of 4600 ELU/ml PROTEX® 6 L) was mixed with 472.8 ml cold water, PEHA (adjusted to pH 7.0, 20 mM final concentration, 4° C.) and glutaraldehyde (133 mM final concentration) was added, mixed well and added to 300 g perlite. Cross-linking of the enzyme occurred by incubating perlite particles in the reaction mixture overnight at room-temperature. Perlite was washed with water, 5 mM phosphate buffer, and water with 3% PEG. Finally, perlite particles were dried over-night at room temperature.

In summary, PROTEX® 6 L was immobilized on 260 g perlite, another small control sample (1 g perlite) was produced the same way, with the exception that no enzyme was added to the reaction mixture. Perlite was then tested for application. The capability of Fel d 1 inactivation was determined.

Example 8

Cleansing liquid prototypes containing functional proteases were developed and tested for inactivation of Fel d 1. Specifically, 1 Liter of cleansing liquid and 50 ml of enzyme concentrate containing active PROTEX® 6 L were manufactured and tested for Fel d 1 inactivation. The prototypes were successful in degradation of Fel d 1. The specifics are discussed in detail below.

First, the concentration of PROTEX® 6 L required for every prototype was determined. The required enzyme concentration is dependent on the amount of Fel d 1 that has to be inactivated by the respective prototype. Based on the data provided by Nestlé Purina, the amount of Fel d 1 in the environment that should be digested by the prototypes is approx. 25 ng/cm2 (=0.25 mg/m2).

For the determination of PROTEX® 6 L concentration that is required for total Fel d 1 digestion, the activity of a PROTEX® 6 L dilution series was analyzed by ELISA. 3.8 U/ml PROTEX® 6 L (Units are based on ethyl-L-lactate assay (ELU), determined by manufacturer Genencore) are capable to completely digest 2.5 µg Fel d 1 under optimal reaction conditions (Tris-HCl buffer, pH 7.8). Based on these calculations, including the initial calculations for the shampoo in Example 9, the concentration of PROTEX® 6 L was adjusted accordingly for the cleansing liquids.

Development of Surface Cleanser Containing PROTEX® 6 L

Based on the Fel d 1 concentration on hard surfaces, the required amount of PROTEX® 6 L was determined and incorporated into the basic cleansing liquid formulation (KAR-001). In detail, water (960 g) was added to a beaker glass, then 10 g phenoxyethanol (preservative), followed by 30 g Zusolat 1008/85 (fatty alcohol available from Zschimmer & Schwarz GmbH & Co KG) and 10 g EUXYL® PE 9010 were added and stirred. If necessary pH had to be adjusted to 8.0 by using NaOH. To this basic formulation (KAR-001) PROTEX® 6 L (9 ml of 4600 ELU/ml PROTEX® 6 L) was added (KAR-001+E). Finally, 1 Liter of surface cleanser KAR-001 containing PROTEX® 6 L (KAR-001+E) as well as 2×1 Liter of surface cleanser without PROTEX® 6 L (KAR-001-E) were produced and tested for application. The capability of Fel d 1 inactivation was determined.

Development of an Enzyme Concentrate Containing PROTEX® 6 L

In addition to the ready-to-use surface cleanser, which already contains PROTEX® 6 L, one could envision another application, which is based on mixing enzyme and liquid surface cleanser just before use.

The advantage is that the enzyme could be mixed with any other surface cleanser, which could either be provided by the customer. In addition storing the enzyme in an optimized liquid formulation and not in surface cleanser formulation could stabilize the enzyme and lead to increased enzymatic stability. Therefore, an enzyme concentrate consisting of 20.times. higher concentrated PROTEX® 6 L (in comparison to the ready-to-use surface cleanser KAR-001+E) and enzyme stabilizer propylene glycol was developed. The capability of Fel d 1 inactivation (after dilution of the 20×KAK-001+E in 1× surface cleanser) was determined.

Example 9

Shampoo prototypes containing functional proteases were developed and tested for inactivation of Fel d 1. Specifically, two cat shampoos (leave-on formulation, 1 Liter each), containing active PROTEX® 6 L was manufactured and tested for Fel d 1 inactivation. All prototypes were successful in degradation of Fel d 1. The specifics for each prototype are discussed in detail below.

First, the concentration of PROTEX® 6 L required for the prototype was determined. The required enzyme concentration is dependent on the amount of Fel d 1 that has to be inactivated by the prototype. The Fel d 1 amount on the cat is approx. 2 µg/mg cat hair (data provided by Nestlé Purina). Since the weight of hair per cat is in average 121 g (Avner D B et al., J Allergy Clin Immunol, 1997) the total amount of Fel d 1 on the cat that should be inactivated by the shampoo is approx. 250 mg For the determination of PROTEX® 6 L concentration that is required for total Fel d 1 digestion, the activity of a PROTEX® 6 L dilution series was analyzed by ELISA. 3.8 U/ml PROTEX® 6 L (Units are based on ethyl-L-lactate assay (ELU), determined by manufacturer Genencore) are capable to completely digest 2.5 µg Fel d 1 under optimal reaction conditions (Tris-HCl buffer, pH 7.8). Next, the activity of PROTEX® 6 L in cat shampoo KFS-002 (see below) was analyzed to determine the activity of PROTEX® 6 L in a shampoo formulation. KFS-002 was chosen as model for initial calculations of PROTEX® 6 L activity in a liquid formulation. It was determined by ELISA that in KFS-002 38.4 U/ml PROTEX® 6 L is required for total inactivation of Fel d 1 (which is approx. 10× higher than in the optimal reaction buffer).

Development of Shampoos Containing PROTEX® 6 L

Several foaming formulations were tested based on amphoteric cocamidopropylbetain (betaine), anionic sodium laurylethersulfate (SLE), anionic sodium lauroyl sarcosinate (SLS), anionic disodium/sodium cocoyl glutamate and nonionic decyl glucoside but not every formulation did provide acceptable results.

Based on the Fel d 1 concentration on the cat, the required amount of PROTEX® 6 L was determined and incorporated into two basic shampoo formulations (KFS-002 and KFS-004a).

In detail, water (980 g) was added to a beaker glass, then 10 g phenoxyethanol (preservative), followed by 10 g betaine (KFS-002) or 10 g SLS (KFS-004a) and 10 g PERLASTAN® L30 were added and stirred. If necessary, pH had to be adjusted to 5.5 (KFS-002) or 7.5 (KFS-004a) by using NaOH. To this basic formulation (KFS-002/004a) 9 ml PROTEX® 6 L (of 4600 ELU/ml PROTEX® 6 L) was added (KFS-002/004a+E). Finally, 1 Liter of shampoo KFS-002 and 1 Liter of shampoo KFS-004a containing PROTEX® 6 L (KFS-002/004a+E) as well as 2×1 Liter of shampoos without PROTEX® 6 L (KFS-002/004a-E) were produced and tested for application. The capability of Fel d 1 inactivation was determined.

The prototypes of Examples 6-9 were studied for inactivation of Fel d 1. All developed prototypes are capable to inactivate application-relevant Fel d 1 amounts.

In the specification, there have been disclosed typical preferred embodiments of the invention and, although specific terms are employed, they are used in a generic and descriptive sense only and not for purposes of limitation, the scope of the invention being set forth in the claims. Numerous modifications and variations of the invention are possible in light of the above teachings. It is therefore to be understood that within the scope of the appended claims the invention may be practiced otherwise than as specifically described.

We claim:

1. A formulation disposed in a cat litter in an amount effective for reducing or eliminating allergenic Fel d 1 from an environment, the formulation comprising a serine protease comprising a subtilisin from at least one species of *Bacillus* selected from the group consisting of *B. licheniformis, B. clausii, B. haloudurans, B. lentus, B. amyloliquefaciens,* and *B. subtilis,* wherein the subtilisin interacts with the Fel d 1 degrades allergenic epitopes on the Fel d 1, wherein the cat litter comprises perlite to which the subtilisin is cross-linked.

2. The formulation of claim 1, wherein the subtilisin is cross-linked to the perlite by a diamine and a dialdehyde.

3. The formulation of claim 1 wherein the subtilisin is from *B. licheniformis*.

4. The formulation of claim 1, further comprising an additive that enhances the efficiency of the subtilisin in degrading the Fel d 1, wherein the additive is cysteine or calcium salt/ions ($Ca^{2+}$), or a combination of cysteine and calcium salt/ions ($Ca^{2+}$).

5. The formulation of claim 1, wherein the subtilisin is recognized as safe for use in foods and cosmetics.

6. The formulation of claim 5, wherein the subtilisin has substantially no interaction with substances selected from: keratin, collagen, elastin, fibronectin, other proteins and fibers or fabric.

7. A method of reducing or eliminating allergenic Fel d 1 from the environment, comprising contacting an element of the environment where Fel d 1 is present with a formulation comprising a serine protease comprising a subtilisin from at least one species of *Bacillus* selected from the group consisting of *B. licheniformis, B. clausii, B. haloudurans, B. lentus, B. amyloliquefaciens,* and *B. subtilis,* wherein the subtilisin interacts with the Fel d 1 and degrades allergenic epitopes on the Fel d 1 thereby reducing or eliminating allergenic Fel d 1 from the environment.

8. The method of claim 7, wherein the Fel d 1 is present on an inanimate surface and the formulation is applied to the surface.

9. The method of claim 7, wherein the Fel d 1 is present in or on an animal that produces Fel d 1 and the formulation is applied to the portion of the animal on which the Fel d 1 is present.

10. The method of claim 9, wherein the Fel d 1 is present on the hair, fur or external skin of the animal or is present in the mouth of the animal.

11. A kit comprising a cat litter comprising a formulation that includes a serine protease comprising a subtilisin from at least one species of *Bacillus* selected from the group consisting of *B. licheniformis, B. clausii, B. haloudurans, B. lentus, B. amyloliquefaciens,* and *B. subtilis,* wherein the subtilisin interacts with the Fel d 1 degrades allergenic epitopes on the Fel d 1, and the kit further comprising instructions for use of the cat litter in reducing or eliminating allergenic Fel dl from the environment, wherein the cat litter comprises perlite to which the subtilisin is cross-linked.

12. The kit of claim 11, wherein the subtilisin is from *B. licheniformis*.

13. The kit of claim 11, wherein the subtilisin is cross-linked to the perlite by a diamine and a dialdehyde.

* * * * *